(12) United States Patent
Park et al.

(10) Patent No.: US 9,354,234 B2
(45) Date of Patent: May 31, 2016

(54) MULTI-FLUORESCENT SUBSTANCE INCLUDING NOVEL COUMARIN DERIVATIVE, AND LED LIGHT SOURCE-BASED MICROFLUORESCENT QUANTITATIVE BIOSENSOR FOR DIAGNOSIS USING SAME

(75) Inventors: Hyun Park, Jeonju-si (KR); Hak Sung Kim, Jeonju-si (KR); Hyun Ok Song, Iksan-si (KR); Chom Kyu Chong, Chungcheongbuk-do (KR); Sung Yeon Kim, Iksan-si (KR)

(73) Assignee: GENBODY INC., Cheonan-si (KR)

( * ) Notice: Subject to any disclaimer, the term of this patent is extended or adjusted under 35 U.S.C. 154(b) by 0 days.

(21) Appl. No.: 14/350,035

(22) PCT Filed: Mar. 5, 2012

(86) PCT No.: PCT/KR2012/001619
§ 371 (c)(1),
(2), (4) Date: Aug. 12, 2014

(87) PCT Pub. No.: WO2013/051769
PCT Pub. Date: Apr. 11, 2013

(65) Prior Publication Data
US 2014/0350227 A1 Nov. 27, 2014

(30) Foreign Application Priority Data

Oct. 5, 2011 (KR) .................. 10-2011-0101273

(51) Int. Cl.
*G01N 33/58* (2006.01)
*C07D 417/04* (2006.01)
*C07D 417/14* (2006.01)
*G01N 33/558* (2006.01)
*G01N 33/569* (2006.01)
*C07D 277/66* (2006.01)

(52) U.S. Cl.
CPC ............ *G01N 33/582* (2013.01); *C07D 277/66* (2013.01); *C07D 417/04* (2013.01); *C07D 417/14* (2013.01); *G01N 33/558* (2013.01); *G01N 33/56905* (2013.01); *G01N 2333/445* (2013.01); *G01N 2458/00* (2013.01)

(58) Field of Classification Search
CPC .................................................... C07D 417/04
USPC ...................................................... 530/391.5
See application file for complete search history.

(56) References Cited

U.S. PATENT DOCUMENTS 4,769,292 A * 9/1988 Tang et al. .................... 428/690

FOREIGN PATENT DOCUMENTS

KR 10-2010-0116287 A 11/2010
KR 10-2011-0097092 A 8/2011

OTHER PUBLICATIONS

Song et al. PLoS One (2012), 7(11), e48459.*

Dawood, F. S. et al. (2009). Emergence of a novel swine-origin influenza A (H1N1) virus in humans. *The New England Journal of Medicine*, 360(25), 2605-2615.
Beigel, J. H. et al. (2005). Avian influenza A (H5N1) infection in humans. *The New England Journal of Medicine*, 353(13), 1374-1385.
Lian, W, et al. (2004). Ultrasensitive detection of biomolecules with fluorescent dye-doped nanoparticles. *Analytical Biochemistry*, 334, 135-144.
Imasaka, T. (1999). Diode lasers in analytical chemistry. *Talanta*, 48, 305-320.
Marais, B. J. et al. (2008). Use of light-emitting diode fluorescence microscopy to detect acid-fast bacilli in sputum. *Clinical Infectious Diseases*, 47(2), 203-207.
Miller, A. R. et al. (2010). Portable, battery-operated, low-cost, bright field and fluorescence microscope. *PLoS One*, 5(8), 1-3.
Wongsrichanalai, C. (2001). Rapid diagnostic techniques for malaria control. *Trends in Parasitology*, 17(7), 307-309.
Cooke, A. H. et al. (1999). Comparison of a parasite lactate dehydrogenase-based immunochromatographic antigen detection assay (Optimal®) with microscopy for the detection of malaria parasites in human blood samples. *The American Society of Tropical Medicine and Hygiene*, 60(2), 173-176.
Notification of Transmittal of the International Search Report and the Written Opinion of the International Searching Authority, or the Declaration, including an International Search Report and Written Opinion of the International Searching Authority, mailed Sep. 14, 2012 in connection with PCT International Application No. PCT/KR2012/001619, filed Mar. 5, 2012 [including English language translation of International Search Report].

* cited by examiner

*Primary Examiner* — Nizal Chandrakumar
(74) *Attorney, Agent, or Firm* — John P. White; Cooper & Dunham LLP

(57) ABSTRACT

The present invention relates to a novel coumarin derivative, to a method for preparing the same, and a multi-fluorescent substance that includes a plurality of the coumarin derivatives and is able to emit light using an LED light source. A novel coumarin derivative multi-fluorescent substance according to the present invention has an optimal emission wavelength band of 512 nm to 590 nm and thereby is effective in improving a signal intensity and stability since light emission using an LED light source is possible.
In addition, higher fluorescence reactivity is exhibited compared to coumarin fluorescent substances known in the related arts since one molecule has a plurality of fluorescent substances, and the problem of the coumarin fluorescent substance possibly binding to a binding site of the antigen of the antibody is solved since fluorescence detection is possible even when a minimum number of fluorescent substance molecules bind to an antibody.
Moreover, the novel coumarin derivative multi-fluorescent substance according to the present invention is suitably used in a fluorescent-linked immunosorbent assay (FLISA) and a rapid fluorescent immunochromatographic test (FICT) as an LED-based microfluorescent quantitative biosensor for diagnosis, therefore, diseases such as malaria may be rapidly and quantitatively analyzed.

3 Claims, 6 Drawing Sheets

MULTI-FLUORESCENT SUBSTANCE INCLUDING NOVEL COUMARIN DERIVATIVE, AND LED LIGHT SOURCE-BASED MICROFLUORESCENT QUANTITATIVE BIOSENSOR FOR DIAGNOSIS USING SAME

CROSS-REFERENCE TO RELATED APPLICATIONS

This application is a §371 national stage of PCT International Application No. PCT/KR2012/001619, filed Mar. 5, 2012, claiming priority of Korean Patent Application No. 10-2011-0101273, filed Oct. 5, 2011, the contents of each of which are hereby incorporated by reference in their entirety.

TECHNICAL FIELD

The present invention relates to a novel coumarin derivative, to a method for preparing the same, and to a multi-fluorescent substance which includes a plurality of the coumarin derivatives and is able to emit light using an LED light source.

BACKGROUND ART

Accurate and rapid diagnosis is one of the important factors in disease management. In particular, rapid diagnosis is very important in the early prevention of infectious diseases such as swine flu, avian influenza, malaria or dengue fever. As an example, many people around the world suffered or died from swine flu or avian influenza infections that occurred in 2009, and this is due to the fact that these infectious pathogens are highly contagious and cause symptoms that can threaten lives (Dawood F S et al., Emergence of a novel swine-origin influenza A (H1N1) virus in human, N Engl J Med, 360(25), pp 2605-2615, 2009; Beigel J H et al., Avian influenza A (H5N1) infection in human, N Engl J Med, 353(13), pp 1374-1385, 2005). In order to prevent the spread of these various infectious diseases in advance, it is required to build a system capable of transmitting the results quickly diagnosed in the field to a central management system in order to systematically monitor the results. In order to rapidly diagnose diseases in the field, it is required to develop biosensors and the like having increased diagnosis accuracy and sensitivity.

Fluorescence technologies have been widely used in various apparatuses for analysis/diagnosis that are utilized in research and clinical diagnoses in the field of biology and medicine (Lian W et al., Ultrasensitive detection of biomolecules with fluorescent dye-doped nanoparticles, Anal Biochem, 334(1), pp 135-144, 2004). This is due to the fact that fluorometry is one of the most sensitive methods that can detect the corresponding organic substances or inorganic substances from an analyte even at a very low concentration. A fluorescent substance-molecule conjugation product (fluorescent bioconjugate) prepared through a simple chemical reaction enables sensitive and quantitative detection of a target substance from an analyte. As a result, numerous organic and inorganic fluorescent substances have been developed to lower costs, secure stability and increase diagnosis sensitivity. However, fluorescent substances that have been developed so far or existing fluorescent substances have a limitation in their use as a biosensor for diagnosis since they still have not overcome deficiencies such as the brightness of a fluorescent substance, the stability of fluorescence duration or severe interference of fluorescence signals. In particular, there is also a disadvantage in that high energy sources are required in order for these fluorescent substances to emit, and a laser diode (LD) always needs to be used.

A laser diode (LD) is a light source that has been used in various analysis apparatuses including diagnostic apparatuses for a long time. However, a laser diode (LD) is more expensive, more inconvenient in operation, has shorter light source life span, and also has a relatively limited light emission range (a wavelength range of approximately 600 nm to 780 nm or 800 nm) compared to a light emitting diode (LED) light source (Imasaka T, Diode lasers in analytical chemistry, Talanta, 48(2), pp 305-320, 1999). In contrast, a light emitting diode (LED) is considered to be a much more efficient light source compared to a laser diode (LD) since an LED has lower costs, stable energy output even with small energy input, longer life span, a very wide light emission wavelength band (a wavelength range of approximately 390 nm to 750 nm, which includes almost the entire wavelength range of an LD). Accordingly, novel fluorescence microscopes for diagnosis that are more economical and have improved diagnosis sensitivity compared to existing microscopes are being developed by replacing the light source of existing fluorescence microscopes for diagnosis with a light emitting diode (LED) (Marais B J et al., Use of light-emitting diode fluorescence microscopy to detect acid-fast bacilli in sputuem, Clin Infect Dis, 47(2), pp 203-207, 2008; Miller A R et al., Portable, battery-operated, low-cost, bright field and fluorescence microscope, Plos One, 5(8), e11890, 2010). Therefore, the development of more efficient, stable and innovative LED-based biosensors for field diagnosis needs to accompany the development of novel fluorescent substances that can emit light using an LED light source with improved signal intensity and stability.

In view of the above, the inventors have developed a novel coumarin derivative multi-fluorescent substance having very improved fluorescence brightness, signal intensity and signal stability.

In addition, the inventors have carried out a fluorescence immunoassay for malaria, which is one of five main diseases highlighted by the World Health Organization (WHO) and a fatal disease with a mortality rate of 5 million worldwide per year, in order to prove the possibility of applying the developed novel coumarin derivative multi-fluorescent substance to the development of an LED-based microfluorescent quantitative biosensor for field diagnosis, that is, to prove its diagnostic usefulness.

A diagnostic method well suited for rapid field diagnosis is an immunochromatographic test (ICT), and most of these have been developed in the form of a dipstick kit. The most widely used dipstick kit for malaria diagnosis worldwide uses a method of detecting *plasmodium* lactate dehydrogenase (pLDH) and *plasmodium* histidine rich protein-2 (pHRP-2) antigen among the specific antigens of malaria. As commercialized products utilizing this method, three products including ICT™ Malaria Pf/Pv (Amrad ICT, Australia), OptiMAL (Flow Inc., U.S.A), and ParaSight™ F (Becton Dickinson, U.S.A) are mainly used, and they all have different target antigens. Chansuda investigated these 3 commercialized products, (Wongsrichanalai, C, Rapid diagnostic techniques for malaria control, Trends Parasitol, 17(7), pp 307-309, 2001), and found out that, while these products have high diagnostic sensitivity of approximately 88% to 98% for *Plasmodium falciparum*, there are problems in that they have diagnostic sensitivity of approximately 75%, 83% and 87%, respectively, for *Plasmodium vivax*. Different from the assertions of the product suppliers, supplementation is necessary since the diagnostic sensitivity is lower than the sensitivity of existing methods, and in particular, the diagnostic sensitivity for *Plasmodium vivax* is only 70 to 80% approximately (Cooke A H. et al., Comparison of a parasite lactate dehydrogenase-based immunochromatographic antigen detection assay (OptiMAL) with microscopy for the detection of malaria parasites in human blood samples, Am J Trop Med Hyg, 60(2), pp 173-176, 1999). In addition, Korean *Plasmodium vivax* often has a long incubation period of normally 6 months to 1 year, as long as 3 years or longer, although it sometimes has a short incubation period of 1 month or less. When this prolonged incubation type occurs, it is difficult to diagnose since it may occur as a subclinical case since the antibody is not formed, or the amount of the antigen is very small. Therefore, there have been demands for the development of sensitive and accurate immunological diagnostic methods capable of diagnosing small amounts of antigens, in addition to the development of novel antibodies capable of early diagnosing a disease.

In view of the above, in order to prepare specific monoclonal antibodies for specific antigens of *Plasmodium falciparum* (PfMSP, PfLDH, PfHRP2), specific antigens of *Plasmodium vivax* (PfMSP, PvLDH, PvHRP2), and antigen determinants, the inventors first produced monoclonal antibodies using polypeptide encoding the LDH genes of *Plasmodium falciparum*, investigated its characteristics, and have verified that diagnosis sensitivity in diagnosing *Plasmodium vivax* and *Plasmodium falciparum* patients can be improved through the production of the monoclonal antibodies for specific antigens and antigen determinants (Korean Patent Application Laid-Open Publication No. 10-2006-0027803).

Furthermore, in order to improve the diagnostic methods for the signs of malaria infection, the inventors have used a fluorescence immunoassay (FIA) that has high sensitivity and enables quantitative analysis, and also enables the development of biosensors for field diagnosis on the basis of these performances.

The inventors have prepared a novel compound of coumarin series as a fluorescent substance to be used in a fluorescence immunoassay, and, considering the problem of low fluorescence detection when only one fluorescent binds to an antibody, have invented the novel coumarin derivative multi-fluorescent substance of the present invention, which is designed such that one molecule has a plurality of fluorescent substances by introducing a linker having a core structure, in order to bind a plurality of fluorescent substances to an antibody.

In addition, the inventors have completed the present invention by verifying that a malaria infection can be effectively diagnosed when conjugating the multi-fluorescent substance to a malaria-specific antibody and using a fluorescence immunoassay (FIA).

Furthermore, the inventors have completed the present invention by verifying that a malaria infection can be diagnosed in the field rapidly and in a quantitative way when conjugating the multi-fluorescent substance to a malaria-specific antibody and using a rapid fluorescent immunochromatographic test (FICT).

DISCLOSURE

Technical Problem

An object of the present invention is to provide a coumarin derivative of Chemical Formula 1, or a salt thereof.

Another object of the present invention is to provide a method for preparing a coumarin derivative of Chemical Formula 1.

Still another object of the present invention is to provide a multi-fluorescent substance prepared by reacting a coumarin derivative of Chemical Formula 1; and a linker having 3, 9 or 27 $N_3$ groups.

Still another object of the present invention is to provide a method for preparing a multi-fluorescent substance prepared by reacting a coumarin derivative of Chemical Formula 1; and a linker having 3, 9 or 27 $N_3$ groups.

Still another object of the present invention is to provide an antibody conjugated with a multi-fluorescent substance prepared by reacting a coumarin derivative of Chemical Formula 1; and a linker having 3, 9 or 27 $N_3$ groups.

Still another object of the present invention is to provide a biosensor that includes an antibody conjugated with a multi-fluorescent substance prepared by reacting a coumarin derivative of Chemical Formula 1; and a linker having 3, 9 or 27 $N_3$ groups.

Technical Solution

In order to accomplish the objectives described above, one aspect of the present invention provides a coumarin derivative of Chemical Formula 1 and a salt thereof.

[Chemical Formula 1]

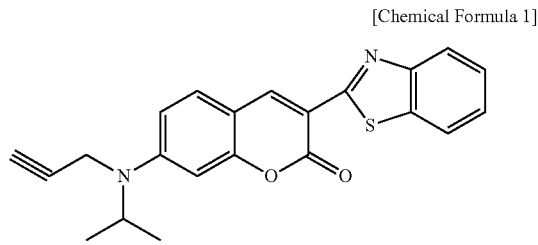 [SMILES: C#CCN(c1ccc2cc(-c3nc4ccccc4s3)c(=O)oc2c1)C(C)C]

The compound of the present invention may be prepared as a salt of the compound and a soluble compound using common methods in the related arts.

As the salt, acid addition salts formed by free acids may be used. Acid addition salts are prepared using common methods, for example, by dissolving a compound in an excess aqueous solution of acids, and then precipitating this salt using a water-miscible organic solvent such as methanol, ethanol, acetone or acetonitrile. Equiomolar amounts of the compound and acid or alcohol in water (for example, glycol monomethylether) are heated, and subsequently, the mixture may be dried by evaporation or the precipitated salts may be suction filtered. At this time, organic acids and inorganic acids may be used as the free acid. As the inorganic acid, hydrochloric acid, phosphoric acid, sulfuric acid, nitric acid, stannic acid or the like may be used, and as the organic acid, methanesulfonic acid, p-toluenesulfonic acid, acetic acid, trifluoroacetic acid, citric acid, maleic acid, succinic acid, oxalic acid, benzoic acid, tartaric acid, fumaric acid, mandelic acid, propionic acid, lactic acid, glycollic acid, gluconic acid, galacturonic acid, glutamic acid, glutaric acid, glucuronic acid, aspartic acid, ascorbic acid, vanillic acid, hydroiodic acid or the like may be used, however, the organic acid and the inorganic acid are not limited thereto.

In addition, pharmaceutically acceptable metal salts may be prepared using bases. Alkali metal or alkaline earth metal salts are obtained by, for example, dissolving the compound in an excess alkali metal hydroxide or alkaline earth metal hydroxide solution, filtering insoluble compound salts, then evaporating the filtrate, and drying. At this time, preparing a sodium, potassium or calcium salt as the metal salt is particularly pharmaceutically suitable, and the silver salt corresponding thereto is obtained by reacting the alkali metal or alkaline earth metal salt with a proper silver salt (for example, silver nitrate).

The salt of the compound of Chemical Formula 1, unless otherwise specified, includes the salts of the acidic or basic groups that can be present in the compound of Chemical Formula 1. For example, the salt includes a sodium, a potassium and a calcium salt of a hydroxyl group, and other salts of an amino group includes hydrochloride, hydrobromide, sulfate, hydrogen sulfate, phosphate, hydrogen phosphate, dihydrogen phosphate, acetate, succinate, citrate, tartrate, lactate, mandelate, methanesulfonate (mesylate), p-toluenesulfonate (tosylate) salts and the like, and these may be prepared through the preparation methods or preparation processes of salts known in the related arts.

Another aspect of the present invention provides a method for preparing the coumarin derivative of Chemical Formula 1. More specifically, a method for preparing the coumarin derivative of Chemical Formula 1, which includes the steps of:

1) preparing a compound of the following Chemical Formula 2 by reacting 3-aminophenol with sodium triacetoxyborohydride and acetone;

2) preparing a compound of the following Chemical Formula 3 by reacting the compound of the following Chemical Formula 2 with N,N-diisopropylethylamine and propargyl chloride;

3) preparing a compound of the following Chemical Formula 4 by reacting the compound of the following Chemical Formula 3 with dimethylformamide and phosphoryl chloride; and 4) preparing a compound of the following Chemical Formula 1 by reacting the compound of the following Chemical Formula 4 with ethyl 2-(benzo[d]thiazol-2-yl)acetate and piperidine, is provided.

In the Step 2), the compound of Chemical Formula 3 is prepared by dissolving the compound of Chemical Formula 2 in toluene, and then reacting the result with N,N-diisopropylethylamine and propargyl chloride.

In the Step 3), the compound of Chemical Formula 4 is prepared by dissolving the compound of Chemical Formula 3 in dimethylformamide, and then reacting the result with dimethylformamide and phosphoryl chloride.

In the Step 4), the compound of Chemical Formula 1 is prepared by dissolving the compound of Chemical Formula 4 in ethanol, and then reacting the result with ethyl 2-(benzo[d]thiazol-2-yl)acetate and piperidine.

The coumarin derivative of Chemical Formula 1 may bind to a linker having $N_3$ groups since the coumarin derivative of Chemical Formula 1 has a propargyl group.

Another aspect of the present invention provides a multi-fluorescent substance prepared by reacting the coumarin derivative of Chemical Formula 1 and a linker having 3, 9 or 27 $N_3$ groups.

More preferably, a multi-fluorescent substance is provided by reacting the coumarin derivative of Chemical Formula 1 and a linker having 3, 9 or 27 $N_3$ groups, and then reacting the result with N-hydroxy succinimide.

The term "linker having 3, 9 or 27 $N_3$ groups" in the present invention means a form having an aromatic ring such as a benzene ring as a core structure and a substituent having a $N_3$ group substituting the aromatic ring.

In the present invention, "N-hydroxy succinimide" is introduced to facilitate the binding of a multi-fluorescent substance to an antibody to form an amide bonding, thereby facilitates the reaction of $NH_2$ of the antibody and the multi-fluorescent substance.

In the present invention, the structure obtained by reacting the linker having $N_3$ groups and N-hydroxy succinimide is preferably a structure of the following Structural Formula 1.

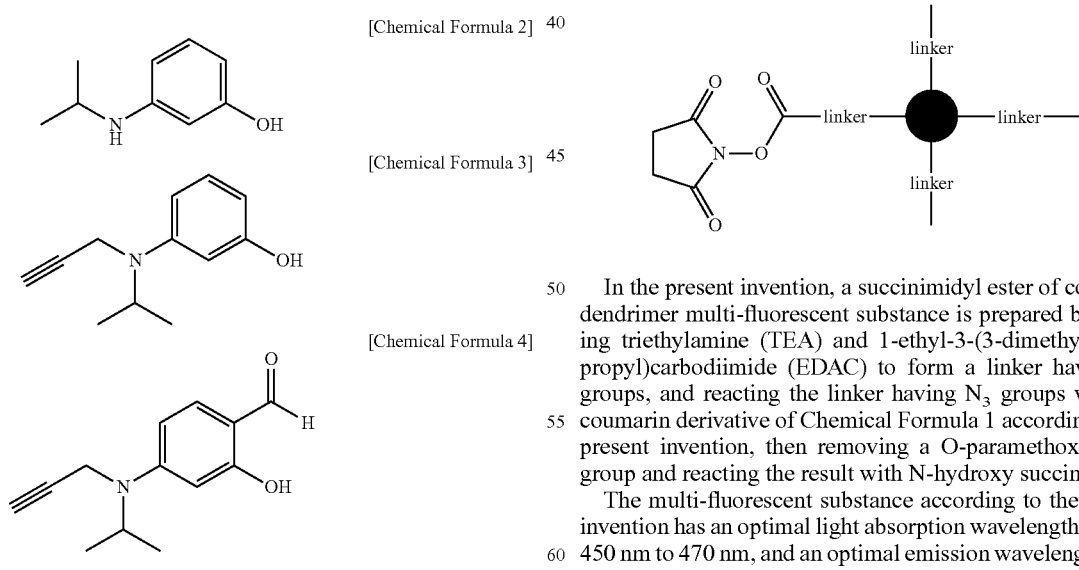

In the present invention, a succinimidyl ester of coumarin dendrimer multi-fluorescent substance is prepared by reacting triethylamine (TEA) and 1-ethyl-3-(3-dimethylaminopropyl)carbodiimide (EDAC) to form a linker having $N_3$ groups, and reacting the linker having $N_3$ groups with the coumarin derivative of Chemical Formula 1 according to the present invention, then removing a O-paramethoxybenzyl group and reacting the result with N-hydroxy succinimide.

The multi-fluorescent substance according to the present invention has an optimal light absorption wavelength band of 450 nm to 470 nm, and an optimal emission wavelength band of 512 nm to 590 nm. Therefore, light emission using an LED light source is possible.

The terms of "excitation wavelength" and "absorption wavelength" are used interchangeably in the present invention. In addition, the terms of "emission wavelength" and "fluoresence wavelength" are also used interchangeably in the present invention.

The reaction formula for preparing the coumarin derivative of Chemical Formula 1 is shown in detail by a diagram in Example 1. The 3-aminophenol compound, which is a starting material, may be readily obtained since the compound may be prepared using various methods known in the related arts or is commercially available.

In other words, the optimal light emission wavelength band of the multi-fluorescent substance according to the present invention belongs to the wavelength band of light emitting diodes (LED) instead of the wavelength band of existing laser diodes (LD), thereby is very suited for the development of LED-based microfluorescent quantitative biosensors for field diagnosis.

The multi-fluorescent substance according to the present invention can be efficiently used in various diagnostic methods, particularly, immunological diagnostic methods based on an antigen-antibody binding, since, while having all the advantages (strong fluorescence brightness and intensity, stably continuous fluorescence signal, and the like) of a quantum dot (QD) that is an inorganic fluorescent substance having the best fluorescence efficiency from among the fluorescent substances that have been developed so far, the multi-fluorescent substance of the present invention is an organic fluorescent substance for which conjugation is carried out by a simple chemical reaction only, which is different from a quantum dot (QD) for which the conjugation process with biomolecules (DNA, protein, antibody, and the like) is relatively inconvenient and complex.

The multi-fluorescent substance according to the present invention has an advantage in that highly-sensitive fluorescence detection is possible. Coumarin dye is a green series fluorescent substance, and a plurality of fluorescent substances need to bind to an antibody in order to make fluorescence detection possible with an antibody of low concentration. However, there has been a problem in that the coumarin dye may bind to a site that binds with an antigen of the antibody since there is no selectivity for a binding site when the coumarin dye is added to the antibody, and therefore the antibody may lose its functions.

In the present invention, in order to solve the above problems, experiments in which 4, 6, 8 and 10 coumarin fluorescent substances bind to one antibody each is carried out as shown in FIG. 3, and ultimately, an optimal result is obtained when 6 coumarin fluorescent substances bind. Therefore, in the present invention, one molecule is designed to have a plurality of fluorescent substances so that fluorescence detection is possible even when a minimum number of fluorescent substance molecules bind to an antibody. In addition, in the present invention, a macro-molecule in which coumarin fluorescent substances are connected is synthesized by selecting a linker having a core structure, which connects the fluorescent substances.

In the present invention, the linker having 3 $N_3$ groups is preferably a linker represented by the compound of the following Chemical Formula 5.

[Chemical Formula 5]

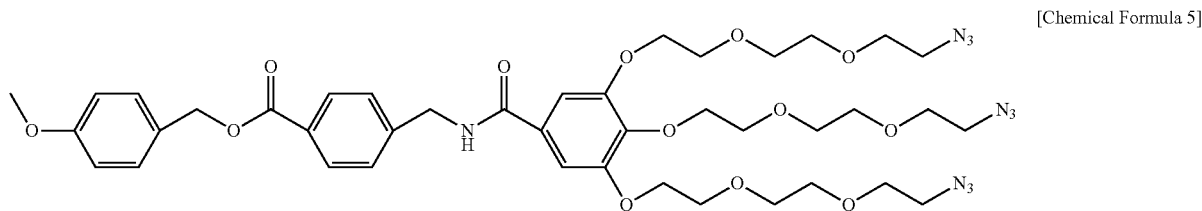 [SMILES: COc1ccc(COC(=O)c2ccc(CNC(=O)c3cc(OCCOCCOCCN=[N+]=[N-])c(OCCOCCOCCN=[N+]=[N-])c(OCCOCCOCCN=[N+]=[N-])c3)cc2)cc1]

Another aspect of the present invention provides a succinimidyl ester of coumarin dendrimer multi-fluorescent substance represented by the following Chemical Formula 6, which is prepared by reacting the linker represented by the compound of Chemical Formula 5 and the coumarin derivative of Chemical Formula 1, then removing O-paramethoxybenzyl group, and reacting the result with N-hydroxy succinimide.

[Chemical Formula 6]

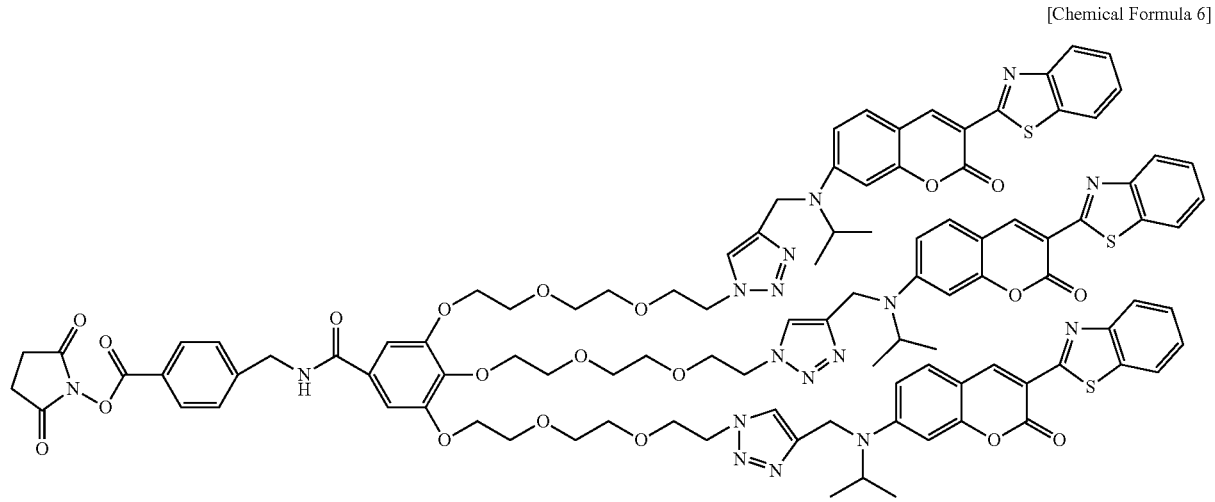 [SMILES: CC(C)N(Cc1cn(CCOCCOCCOc2cc(C(=O)NCc3ccc(C(=O)ON4C(=O)CCC4=O)cc3)cc(OCCOCCOCCn3cc(CN(c4ccc5cc(-c6nc7ccccc7s6)c(=O)oc5c4)C(C)C)nn3)c2OCCOCCOCCn2cc(CN(c3ccc4cc(-c5nc6ccccc6s5)c(=O)oc4c3)C(C)C)nn2)nn1)c1ccc2cc(-c3nc4ccccc4s3)c(=O)oc2c1]

Another aspect of the present invention provides a method for preparing the linker having 3 $N_3$ groups of Chemical Formula 5. More specifically, a method for preparing the compound represented by Chemical Formula 5, which includes the steps of:

1) preparing a compound of the following Chemical Formula 8 by reacting a compound of the following Chemical Formula 7 with sodium azide;

2) preparing a compound of the following Chemical Formula 9 by reacting the compound of the following Chemical Formula 8 with tosyl chloride, 4-dimethylaminopyridine and triethylamine;

3) preparing a compound of the following Chemical Formula 11 by reacting the compound of the following Chemical Formula 9 with a compound of the following Chemical Formula 10, $K_2CO_3$ and tetrabutylammonium bromide;

4) preparing a compound of the following Chemical Formula 12 by reacting the compound of the following Chemical Formula 11 with LiOH;

5) preparing a compound of the following Chemical Formula 14 by reacting the compound of the following Chemical Formula 12 with a compound of the following Chemical Formula 13, triethylamine and 1-ethyl-3-(3-dimethylamino-propyl)carbodiimide;

6) preparing a compound of the following Chemical Formula 15 by reacting the compound of the following Chemical Formula 14 with LiOH; and 7) preparing the compound of Chemical Formula 5 by reacting the compound of the following Chemical Formula 15 with para-methoxybenzyl bromide and sodium bicarbonate, is provided.

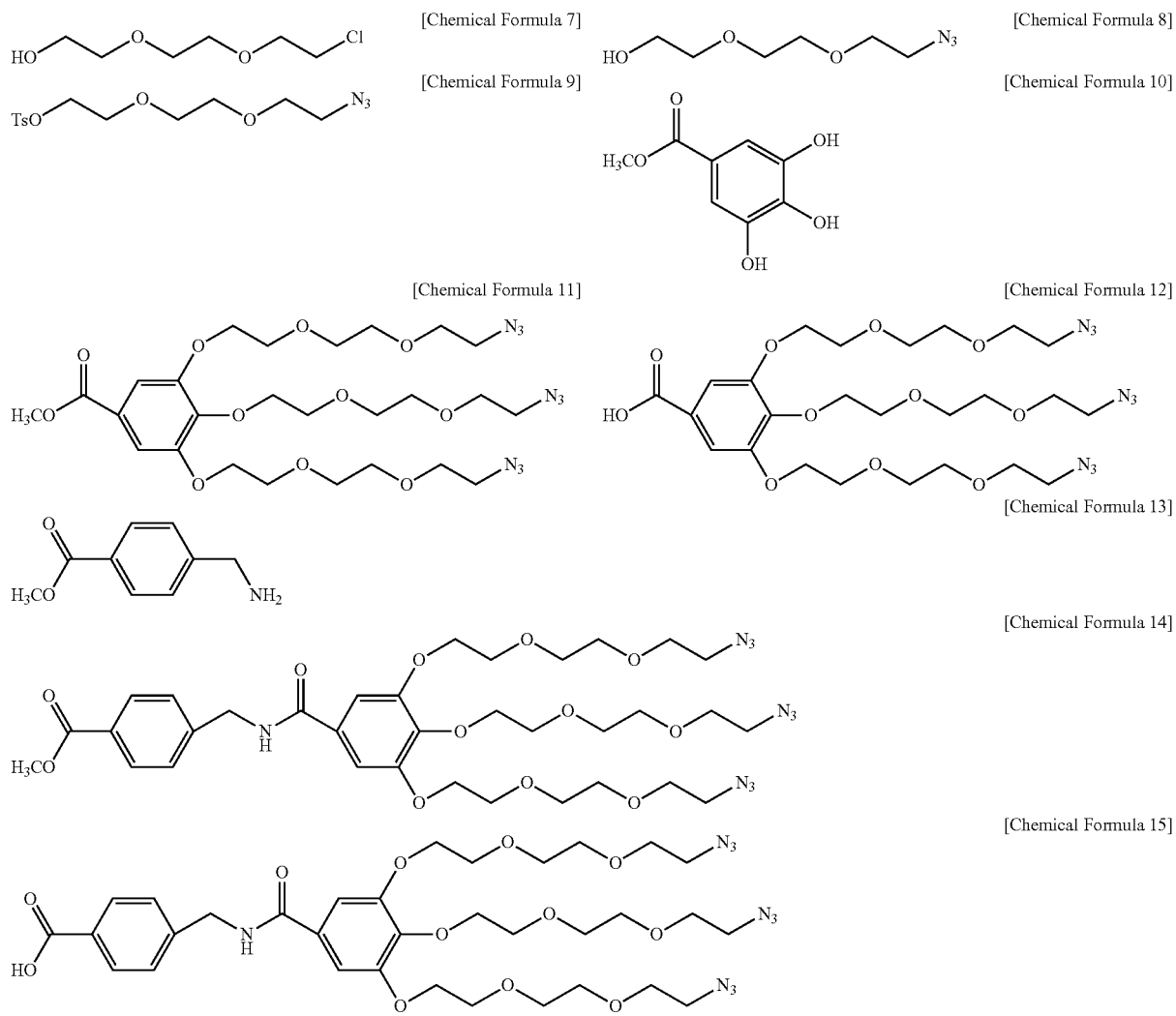

The reaction formula for preparing the linker of Chemical Formula 5 having 3 $N_3$ groups is shown in detail by a diagram in Example 2. The compound of Chemical Formula 7, which is a starting material, may be readily obtained since the compound may be prepared using various methods known in the related arts or is commercially available.

In the Step 1), the compound of Chemical Formula 8 is prepared by dissolving the compound of Chemical Formula 7 in dimethylformamide, and then reacting the result with sodium azide.

In the Step 2), the compound of Chemical Formula 9 is prepared by dissolving the compound of Chemical Formula 8 in methylene chloride, and then reacting the result with tosyl chloride, 4-dimethylaminopyridine and triethylamine.

In the Step 3), the compound of Chemical Formula 11 is prepared by dissolving the compound of Chemical Formula 9 in acetone, and then reacting the result with the compound of Chemical Formula 10, $K_2CO_3$ and tetrabutylammonium bromide.

In the Step 4), the compound of Chemical Formula 12 is prepared by dissolving the compound of Chemical Formula 11 in tetrahydrofuran, and then reacting the result with LiOH.

In the Step 5), the compound of Chemical Formula 14 is prepared by dissolving the compound of Chemical Formula 12 in methylene chloride, and then reacting the result with the compound of Chemical Formula 13, triethylamine (TEA) and 1-ethyl-3-(3-dimethylaminopropyl)carbodiimide (EDAC).

In the Step 6), the compound of Chemical Formula 15 is prepared by dissolving the compound of Chemical Formula 14 in tetrahydrofuran, and then reacting the result with LiOH.

In the Step 7), the compound of Chemical Formula 5 is prepared by dissolving the compound of Chemical Formula 15 in dimethylformamide, and then reacting the result with para-methoxybenzyl bromide and sodium bicarbonate.

Another aspect of the present invention provides a method for preparing the succinimidyl ester of coumarin dendrimer of Chemical Formula 6. More specifically, a method for preparing the succinimidyl ester of coumarin dendrimer of Chemical Formula 6, which includes the steps of:

1) preparing a compound of the following Chemical Formula 16 by reacting the compound of Chemical Formula 5 and the coumarin derivative of Chemical Formula 1 of claim 1 with $CuSO^4.5H_2O$ and sodium ascorbate;

2) preparing a compound of the following Chemical Formula 17 by reacting the compound of the following Chemical Formula 16 with trifluoroacetic acid; and 3) preparing the compound of Chemical Formula 6 by reacting the compound of the following Chemical Formula 17 with N-hydroxy succinimide and 1-ethyl-3-(3-dimethylaminopropyl)carbodiimide, is provided.

[Chemical Formula 16]

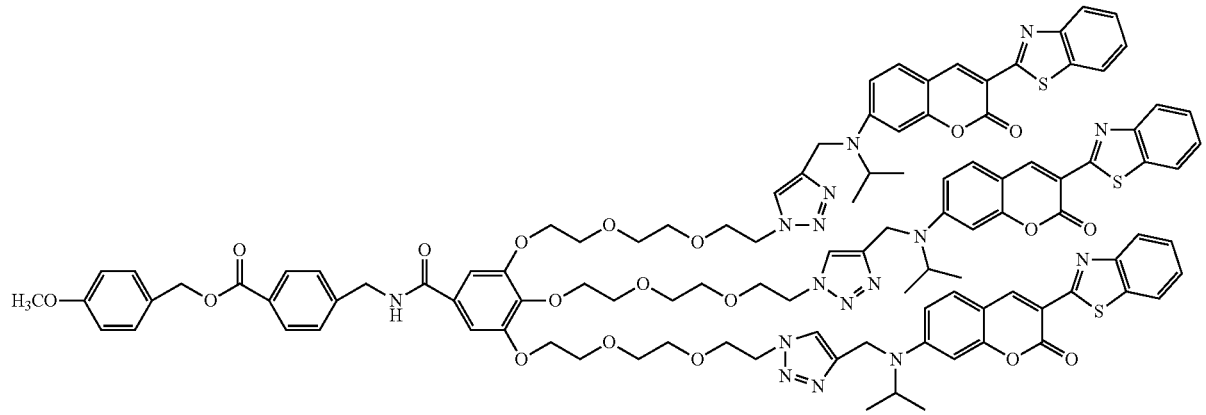

[Chemical Formula 17]

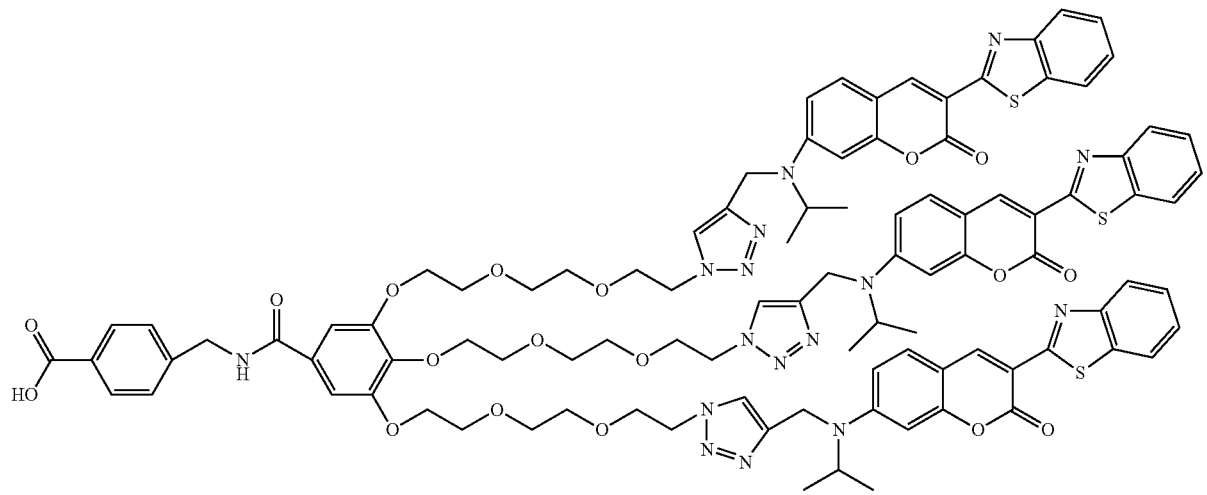

The reaction formula for preparing the succinimidyl ester of coumarin dendrimer of Chemical Formula 6 is shown in detail by a diagram in Example 3.

In the Step 1), the compound of Chemical Formula 16 is prepared by dissolving the compound of Chemical Formula 5 and the coumarin derivative of Chemical Formula 1 of claim 1 in methylene chloride and distilled water, and then reacting the result with $CuSO_4.5H_2O$ and sodium ascorbate.

In the Step 2), the compound of Chemical Formula 17 is prepared by dissolving the compound of Chemical Formula 16 in methylene chloride, and then reacting the result with trifluoroacetic acid.

In the Step 3), the compound of Chemical Formula 6 is prepared by dissolving the compound of Chemical Formula 17 in methylene chloride, and then reacting the result with N-hydroxy succinimide and 1-ethyl-3-(3-dimethylaminopropyl)carbodiimide.

In the present invention, the linker having 9 $N_3$ groups is preferably a linker represented by the following Chemical Formula 18.

[Chemical Formula 18]
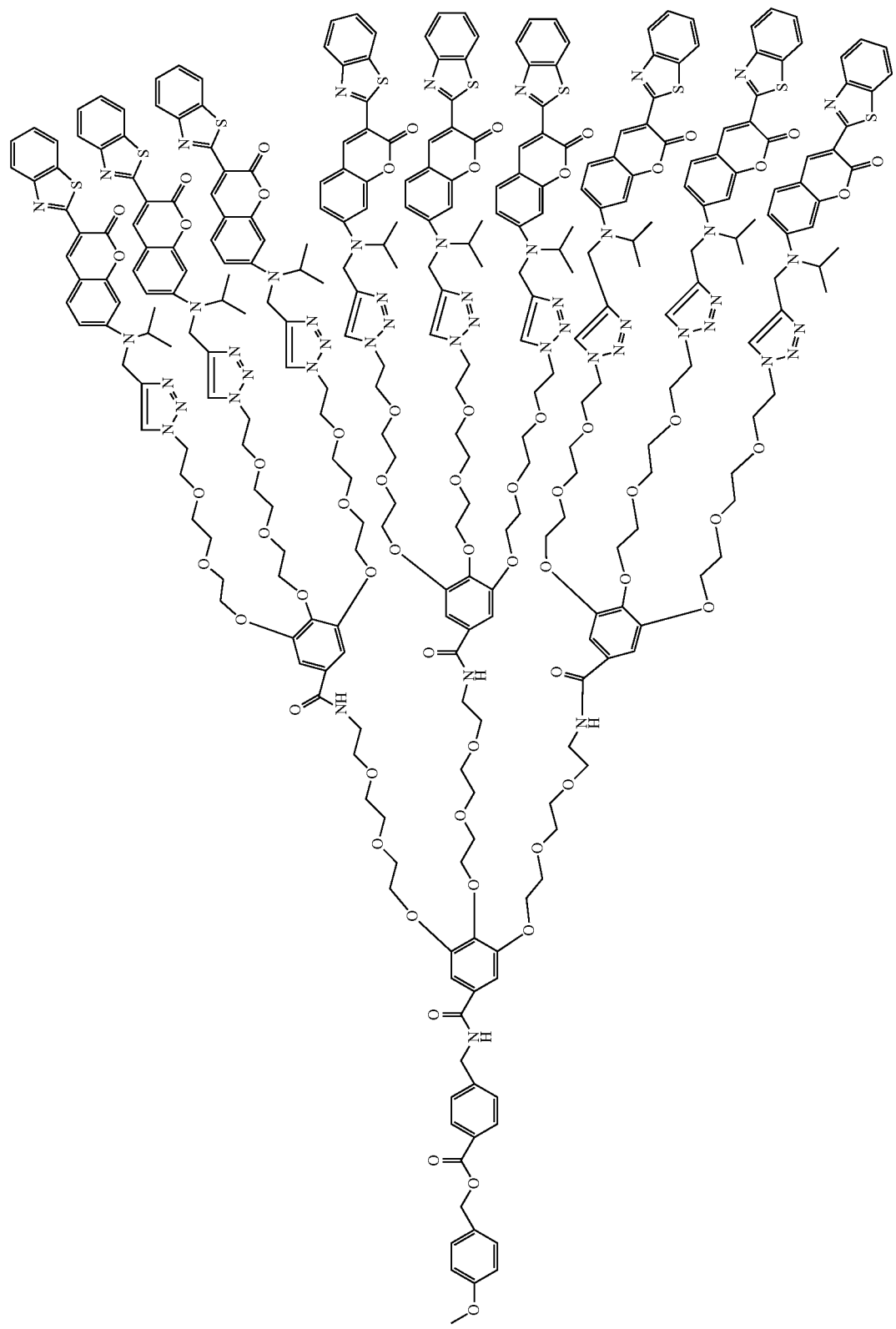

Another aspect of the present invention provides a succinimidyl ester of coumarin dendrimer multi-fluorescent substance represented by the following Chemical Formula 19 prepared by reacting the linker represented by the compound of Chemical Formula 18 and the coumarin derivative of Chemical Formula 1, and then removing O-paramethoxybenzyl group and reacting the result with N-hydroxy succinimide.

[Chemical Formula 19]
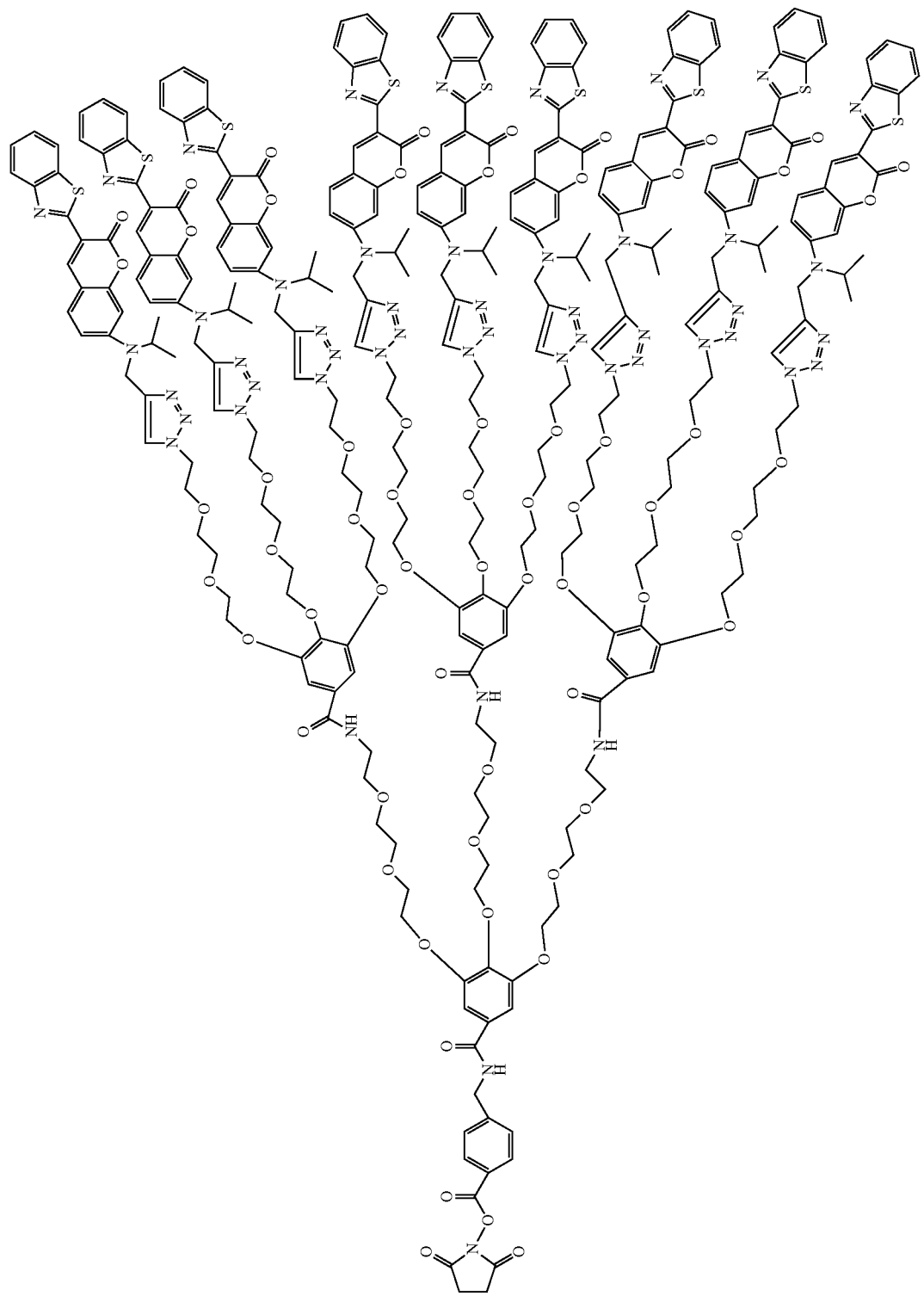

In the present invention, the linker having 27 $N_3$ groups is preferably a linker represented by the following Chemical Formula 20.

[Chemical Formula 20]
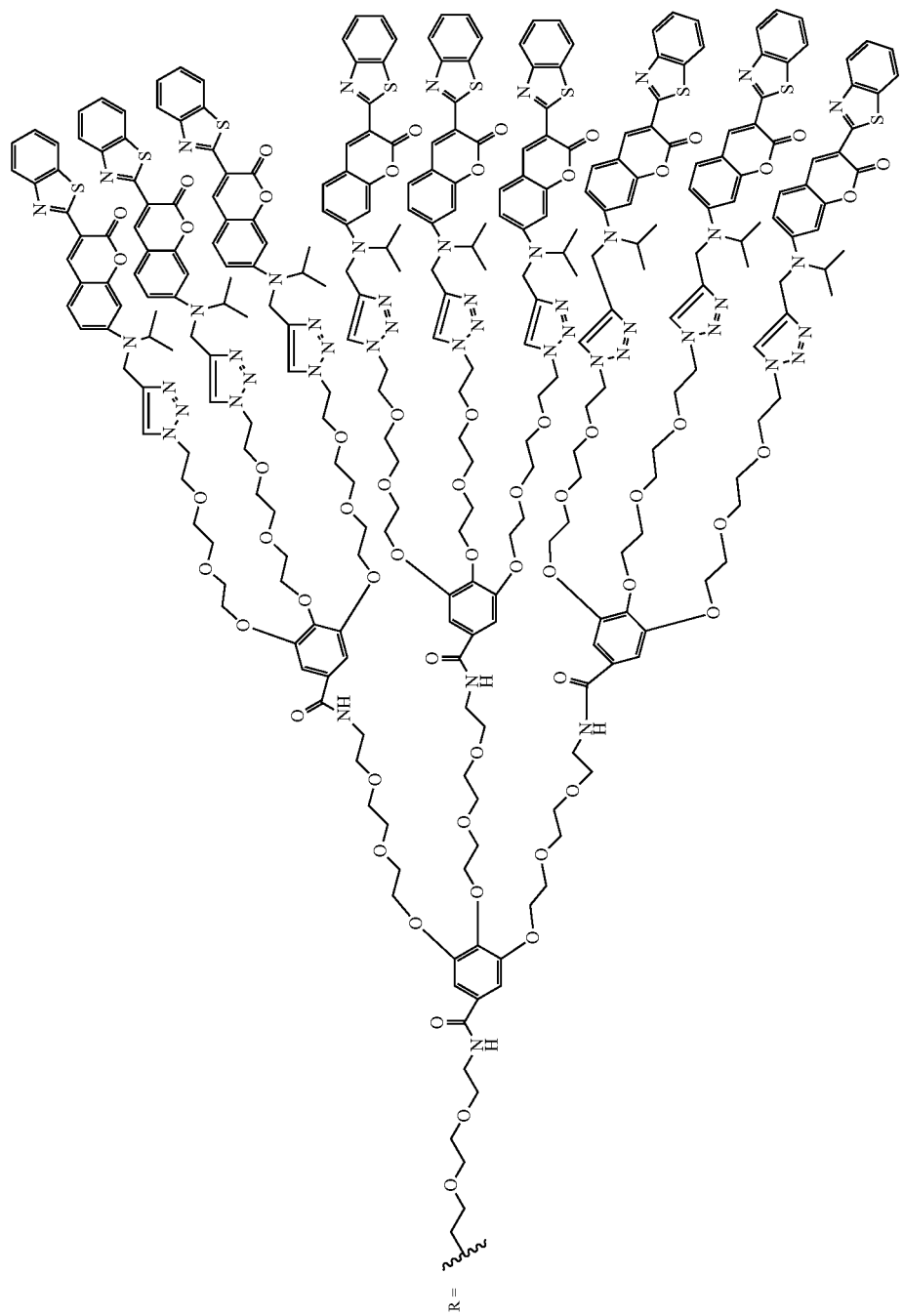
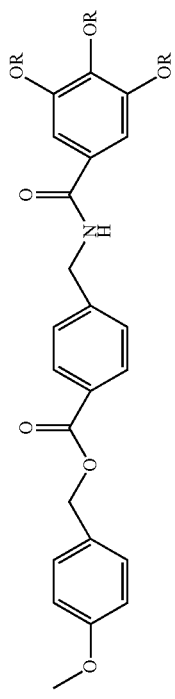

Another aspect of the present invention provides a succinimidyl ester of coumarin dendrimer multi-fluorescent substance represented by the following Chemical Formula 21 by reacting the linker represented by the compound of Chemical Formula 20 and the coumarin derivative of Chemical Formula 1 of the present invention, and then removing O-paramethoxybenzyl group and reacting the result with N-hydroxy succinimide.

[Chemical Formula 21]
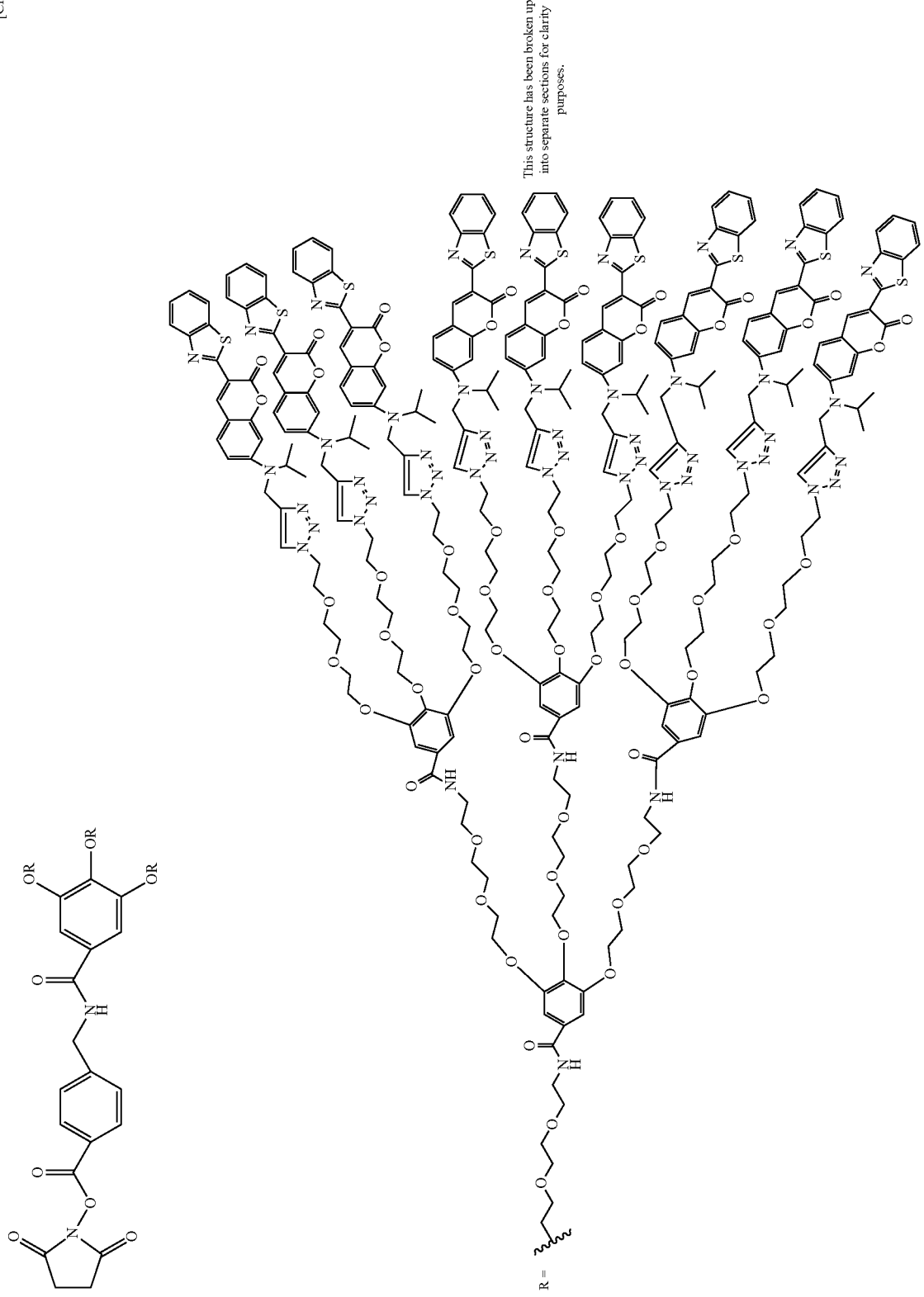

Another aspect of the present invention provides an antibody conjugated with the novel coumarin derivative multi-fluorescent substance. The succinimidyl ester of coumarin dendrimer according to the present invention may form a bound substance with an antibody through a conjugation reaction. In this conjugation reaction, lysine of the antibody (including a —$NH_2$ group) and the ester group are conjugated and bind in the form of an amide bond. The bound substance of an immunosubstance and a fluorescent substance formed from a conjugation reaction is an essential requisite in using a microfluorescent quantitative biosensor.

Another aspect of the present invention provides a microfluorescent quantitative biosensor that includes an antibody conjugated with a multi-fluorescent substance. The coumarin derivative of Chemical Formula 1 is a fluorescent substance having a coumarin skeleton, and may be used in an enzyme-linked immunosorbent assay (ELISA) and a rapid fluorescent immunochromatographic test (FICT), since effective detection using a light-emitting diode (LED) light source is possible.

In the present invention, the microfluorescent quantitative biosensor means a sensor capable of sensing biosignals of a human being by analyzing fluorescence signals. A biosensor is an apparatus that directly measures produced substances at room temperature and under atmospheric pressure by carrying out a reaction identical to that of an in-vivo reaction using a substance that has excellent recognition function for specific chemical substances among the biometerials present in an organism. In the present invention, the concept of the microfluorescent quantitative biosensor includes a fluoroimmunoassay kit.

Specifically, in the examples of the present invention, a fluorescence-linked immunosorbent assay (FLISA) is carried out in order to verify the reactivity of the monoclonal antibody-fluorescent substance conjugation product.

A fluorescence-linked immunosorbent assay (FLISA), like enzyme-linked immunosorbent assay (ELISA), uses fluorimetry and thereby has short analysis time and may measure the substances to be diagnosed in large quantities. In addition, a fluorescence-linked immunosorbent assay is generally known to have more superior sensitivity and specificity compared to an enzyme-linked immunosorbent assay.

A rapid fluorescence immunochromatographic test (FICT) is a technology that has high accuracy, and a method in which an immunosubstance (for example, antigen or antibody) is fixed on a stationary phase such as a membrane, a fluorescent substance-immunosubstance is used as a mobile phase, and after the reaction is complete, a target substance may be quantitatively measured using the signals passing through a fluorescent substance. This method is useful for emergency field diagnosis since the results are quickly obtained, the instructions are simple, and the quantitation of an output is possible, however, the types of fluorescent substances that can be used in this system are limited, and there is a disadvantage in that a fairly expensive light source needs to be used depending on the excitation and the light emission wavelength band (wavelength).

The novel coumarin derivative multi-fluorescent substance of the present invention is a fluorescent substance suited for a fluorescence-linked immunosorbent assay and a rapid fluorescence immunochromatographic test, and exhibits high fluorescence reactivity since one molecule has a plurality of fluorescent substances.

Various diseases can be analyzed rapidly and quantitatively by using a biosensor that includes the novel coumarin derivative multi-fluorescent substance according to the present invention. More preferably, a malaria disease can be analyzed rapidly and quantitatively. According to specific examples of the present invention, a fluorescence-linked immunosorbent assay (FLISA) was carried out for malaria antigens using the succinimidyl ester of coumarin dendrimer of Chemical Formula 6. As a result, the novel coumarin derivative multi-fluorescent substance-antibody conjugation product of the present invention exhibits high reactivity for malaria antigens.

Advantageous Effects

A novel coumarin derivative multi-fluorescent substance according to the present invention has an optimal emission wavelength band of 512 nm to 590 nm and thereby is effective in improving a signal intensity and stability since light emission using an LED light source is possible.

In addition, higher fluorescence reactivity is exhibited compared to coumarin fluorescent substances known in the related arts since one molecule has a plurality of fluorescent substances, and the problem of the coumarin fluorescent substance possibly binding to a binding site of the antigen of the antibody is solved since fluorescence detection is possible even when a minimum number of fluorescent substance molecules bind to an antibody.

Moreover, the novel coumarin derivative multi-fluorescent substance according to the present invention is suitably used in a fluorescent-linked immunosorbent assay (FLISA) and a fluorescent immunochromatographic test (FICT), therefore, diseases such as malaria may be rapidly and quantitatively analyzed.

MODE FOR DISCLOSURE

Figure 1:
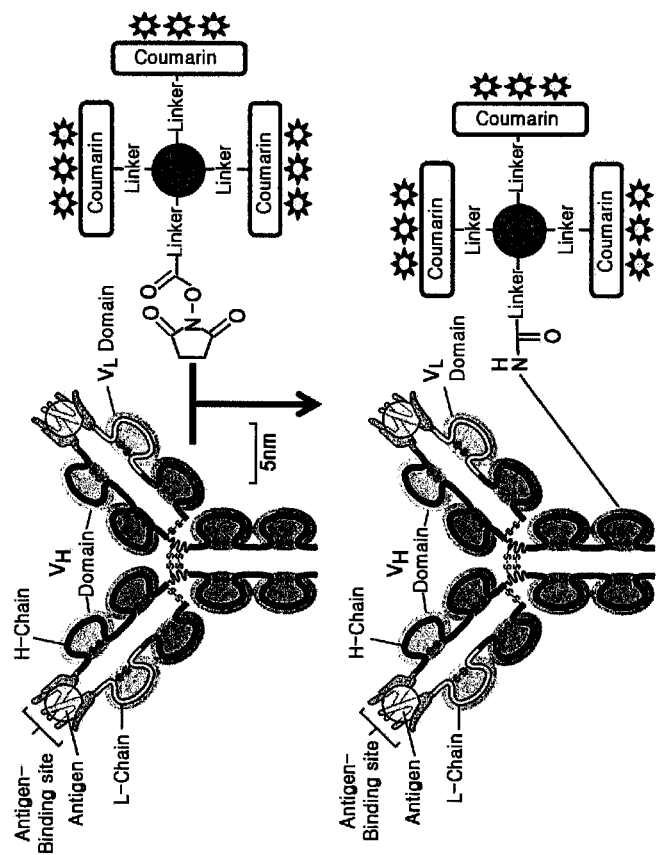
FIG. 1 is a schematic diagram that shows the binding method of an antibody and a multi-fluorescent substance having 3 coumarin fluorescent substances.

Hereinafter, the present invention will be described in more detail with reference to examples. However, these examples are for illustrative purposes only, and the scope of the invention is not limited thereto.

EXAMPLE 1

Synthesis of Coumarin Derivative of Chemical Formula 1

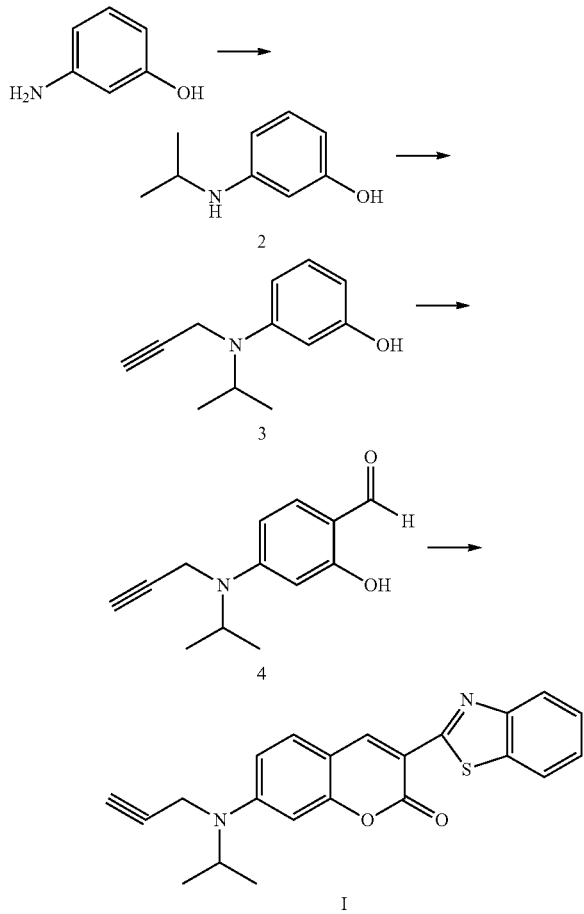

Synthesis processes of a novel coumarin derivative are as follows.

1-1. Synthesis of 3-(isopropylamino)phenol Compound of Chemical Formula 2

After THF (50 mL) suspension of sodium borohydride (2.70 g, 71.37 mmol) was cooled to 0° C. and glacial acetic acid (12.46 ml, 115.3 mmol) was slowly added thereto, the mixture was stirred, warmed to room temperature, and then stirred overnight. 3-aminophenol (2.0 g, 18.32 mmol) and acetone (13.42 mL, 183.2 mmol) were added consecutively to the sodium triacetoxyborohydride solution prepared as above and the result was stirred for 12 hours. The reaction mixture was washed with a saturated sodium bicarbonate solution (30 mL), distilled water (30 mL) and saturated salted water (20 mL) consecutively. The organic layer was dried with anhydrous sodium sulfate, filtered and vacuum distilled, and the residue obtained was column chromatographed on silica gel (hexane/ethyl acetate (4:1)) to give 3-(isopropylamin)phenol (2.16 g, 78%). $^1$H NMR (500 MHz, CDCl$_3$) d 6.99 (t, 1H, J=8.25 Hz), 6.12-6.17 (m, 2H), 6.07 (t, 1H, J=2.3 Hz), 3.54-3.61 (m, 1H), 1.19 (d, 6H, J=6.4 Hz); $^{13}$C NMR (125 MHz, CDCl$_3$) d 156.7, 149.1, 130.2, 106.5, 103.9, 99.9, 44.3, 23.0 (2).

1-2. Synthesis of 3-(Isopropyl(prop-2-ynyl)amino)phenol Compound of Chemical Formula 3

To a solution in which the 3-(isopropylamin)phenol (2.0 g, 13.22 mmol) compound of Chemical Formula 2 was dissolved in toluene (15 mL), N,N-diisopropylethylamine (5.75 mL, 33.05 mmol), which is Hunig's base, and propargyl chloride (2.36 mL, 33.05 mmol) were added in order at room temperature. The reaction mixture was stirred for 10 hours at 50° C., and then was cooled to room temperature. The post-reaction mixture obtained as above was partitioned to ethyl acetate (30 mL) and distilled water (30 mL). The organic layer was separated, washed with saturated salted water (10 mL), dried with anhydrous sodium sulfate, filtered and vacuum distilled, and the residue obtained was column chromatographed on silica gel (hexane/ethyl acetate (6:1)) to give 3-(isopropyl(prop-2-ynyl)amino)phenol (2.22 g, 89%). $^1$H NMR (500 MHz, CDCl$_3$) d 7.03 (t, 1H, J=8.2 Hz), 6.40 (dd, 1H, J=8.2 Hz), 6.32 (s, 1H), 6.16 (dd, 1H, J=7.7 Hz), 3.98-4.07 (m, 1H), 3.85 (d, 2H, J=2.2 Hz), 2.10 (t, 1H, J=2.3 Hz), 1.18 (d, 6H, J=6.9 Hz); $^{13}$C NMR (125 MHz, CDCl$_3$) d 156.7, 149.8, 130.1, 106.4, 104.3, 100.7, 82.2, 71.1, 48.8, 33.6, 20.1 (2).

1-3. Synthesis of 2-Hydroxy-4-(isopropyl(prop-2-ynyl)amino)benzaldehyde Compound of Chemical Formula 4

After DMF (13.30 mL, 172.6 mmol) was cooled to 0° C. and POCl$_3$ (2.68 mL, 28.79 mmol) was added dropwise thereto, the mixture was stirred for 20 minutes, warmed to room temperature, and then stirred for 1 hour. To this reactant, a solution in which the 3-(isopropyl(prop-2-ynyl)amino)phenol compound of Chemical Formula 3 (2.18 g, 11.51 mmol) was dissolved in DMF (10 mL) was added, and then the mixture was stirred for 12 hours. Distilled water (30 mL) was added to the post-reaction mixture, and the result was neutralized to between pH 7 and 8 by adding sodium bicarbonate solid. After this mixture was partitioned to acetic acid (100 mL) and distilled water (30 mL), the organic layer was separated, washed with saturated salted water (10 mL), dried with anhydrous sodium sulfate, filtered and vacuum distilled, and the residue obtained was column chromatographed on silica gel (hexane/ethyl acetate (7:1)) to give 2-hydroxy-4-(isopropyl(prop-2-ynyl)amino)benzaldehyde (2.05 g, 82%). $^1$H NMR (500 MHz, CDCl$_3$) d 11.52 (s, 1H), 9.55 (s, 1H), 7.33 (d, 1H, J=8.7 Hz), 6.46 (dd, 1H, J=2.3, 8.7 Hz), 6.29 (d, 1H, J=2.3 Hz), 4.19-4.22 (m, 1H), 3.98 (d, 2H, J=2.7 Hz), 2.23 (t, 1H, J=2.7 Hz), 1.29 (d, 6H, J=6.9 Hz); $^{13}$C NMR (125 MHz, CDCl$_3$) d 192.7, 164.2, 154.7, 135.3, 112.4, 105.4, 98.5, 80.4, 72.0, 49.1, 33.3, 20.2 (2).

1-4. Synthesis of 3-(Benzo[d]thiazol-2-yl)-7-(isopropyl(prop-2-ynyl)amino)-2H-chromen-2-one Compound of Chemical Formula 1

To a solution in which the 2-hydroxy-4-(isopropyl(prop-2-ynyl)amino)benzaldehyde (1.8 g, 8.28 mmol) compound of Chemical Formula 4 was dissolved in ethanol (15 mL), ethyl 2-(benzo[d]thiazol-2-yl)acetate (1.83 g, 8.28 mmol) and piperidine (1.63 mL, 16.56 mmol) were added consecutively at room temperature. The reaction mixture was heated under reflux for 2 hours, cooled to room temperature, and 3-(benzo[d]thiazol-2-yl)-7-(isopropyl(prop-2-ynyl)amino)-2H-chromen-2-one (1.54 g, 50%) was obtained by filtering the precipitated solid. $^1$H NMR (500 MHz, CDCl$_3$) d 8.94 (s, 1H), 8.02 (d, 1H, J=8.2 Hz), 7.94 (d, 1H, J=7.8 Hz), 7.54 (d, 1H, J=8.7 Hz), 7.47-7.50 (m, 1H), 7.35-7.38 (m, 1H), 6.88 (dd, 1H, J=2.3, 8.7 Hz), 6.80 (d, 1H, J=2.3 Hz), 4.21-4.26 (m, 1H), 4.04 (d, 2H, J=2.3 Hz), 2.26 (t, 1H, J=2.2 Hz), 1.34 (d, 6H, J=6.4 Hz); $^{13}$C NMR (125 MHz, CDCl$_3$) d 161.5, 161.0, 156.7, 152.6, 152.4, 142.0, 136.4, 130.6, 126.2, 124.7, 122.3, 121.7, 113.9, 111.0, 109.8, 98.8, 80.0, 72.3, 49.5, 33.5, 20.2 (2).

EXAMPLE 2

Synthesis of Linker Having Reactive Group of Chemical Formula 5 Bindable to 3 Coumarin Derivatives

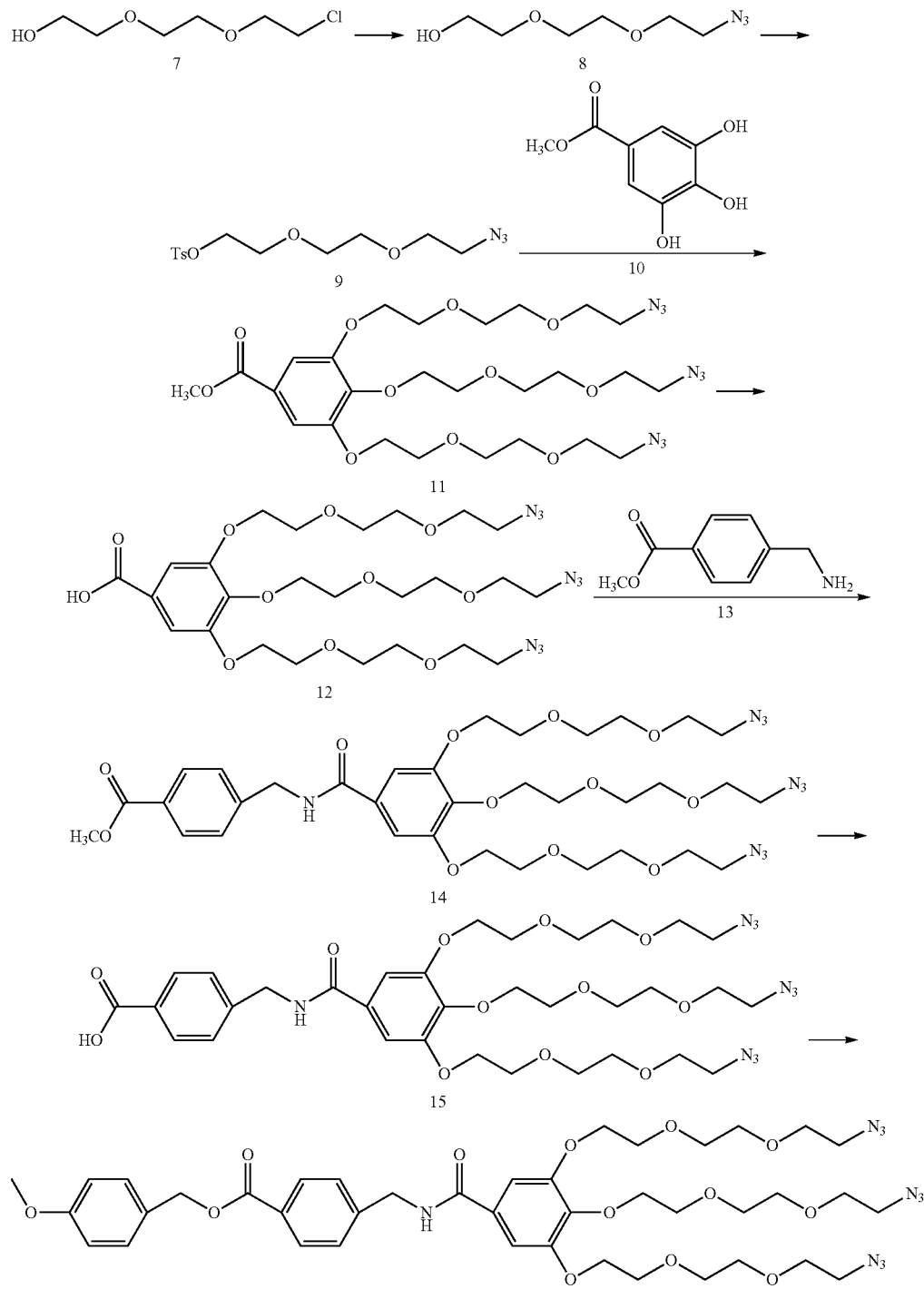

Synthesis processes of a linker having a reactive group bindable to 3 coumarin derivatives are as follows.

2-1. Synthesis of 2-(2-(2-Azidoethoxy)ethoxy)ethanol Compound of Chemical Formula 8

To a solution in which 2-(2-(2-chloroethoxy)ethoxy)ethanol (3.48 g, 20.63 mmol) of Chemical Formula 7 was dissolved in DMF (15 mL), sodium azide (4.02 g, 61.89 mmol) was added at room temperature, and the mixture was heated to 100° C. and stirred for 12 hours. After the reaction, DMF was removed by vacuum distillation, and the residue was partitioned to distilled water (40 mL) and ethyl acetate (150 mL). The organic layer was separated, washed with saturated salted water (15 mL), dried with anhydrous sodium sulfate, and vacuum distilled, and the residue obtained was column chromatographed on silica gel (hexane/ethyl acetate (2:1)) to give 2-(2-(2-azidoethoxy)ethoxy)ethanol (3.05 g, 84%). $^1$H NMR (500 MHz, CDCl$_3$) δ 3.72-3.74 (m, 2H), 3.65-3.69 (m, 6H), 3.60-3.62 (m, 2H), 3.39 (t, 2H, J=5.0 Hz).

2-2. Synthesis of 2-(2-(2-Azidoethoxy)ethoxy)ethyl 4-methylbenzenesulfonate Compound of Chemical Formula 9

To a solution in which the 2-(2-(2-azidoethoxy)ethoxy)ethanol (3.05 g, 17.40 mmol) compound of Chemical Formula 8 was dissolved in methylene chloride (15 mL), 4-dimethylaminopyridine (DMAP) (212.6 mg, 1.74 mmol), triethylamine (TEA) (7.28 mL, 52.20 mmol) and tosyl chloride (3.98 g, 20.88 mmol) were added consecutively at room temperature. The post-reaction mixture obtained after stirring the reaction mixture for 12 hours at room temperature was partitioned to distilled water (40 mL) and ethyl acetate (120 mL). The organic layer was separated, washed with saturated salted water (15 mL), dried with anhydrous sodium sulfate, and vacuum distilled to give 2-(2-(2-azidoethoxy)ethoxy)ethyl 4-methylbenzenesulfonate (5.15 g, 90%). $^1$H NMR (500 MHz, CDCl$_3$) δ 7.79 (d, 2H, J=8.2 Hz), 7.33 (d, 2H, J=8.2 Hz), 4.15 (t, 2H, J=5.0 Hz), 3.69 (t, 2H, J=5.0 Hz), 3.63 (t, 2H, J=5.5 Hz), 3.59 (s, 4H), 3.36 (t, 2H, J=5.0 Hz), 2.44 (s, 3H); $^{13}$C NMR (125 MHz, CDCl$_3$) δ 144.9, 133.0, 129.9 (2), 128.0 (2), 70.8, 70.7, 70.1, 69.3, 68.8, 50.7, 21.7.

2-3. Synthesis of Methyl Gallate Compound of Chemical Formula 10

To a solution in which gallic acid (5.0 g, 29.39 mmol) was dissolved in methanol (25 mL), concentrated sulfuric acid (0.5 mL) and trimethyl orthoformate (3.21 mL, 88.17 mmol) were added consecutively at room temperature. The reaction mixture was heated under reflux for 10 hours, cooled to room temperature, and methanol was removed by vacuum distillation. To the residue obtained as above, distilled water (10 mL) was added, and the precipitated solid was filtered to give methyl gallate (5.15 g, 95%). $^1$H NMR (500 MHz, DMSO-D6) δ 9.29 (s, 2H), 8.96 (s, 1H), 6.92 (s, 2H), 3.73 (s, 3H).

2-4. Synthesis of Methyl 3,4,5-Tris(2-(2-(2-azidoethoxy)ethoxy)ethoxy)benzoate Compound of Chemical Formula 11

To a solution in which the 2-(2-(2-azidoethoxy)ethoxy)ethyl 4-methylbenzenesulfonate (4.80 g, 14.57 mmol) compound of Chemical Formula 9 was dissolved in acetone (15 mL), K$_2$CO$_3$ (2.05 g, 14.85 mmol), the methyl gallate (650.9 mg, 3.53 mmol) compound of Chemical Formula 10 and tetrabutylammonium bromide (25 mg) were added consecutively at room temperature. The reaction mixture was heated under reflux for 17 hours, cooled to room temperature, and partitioned to distilled water (40 mL) and ethyl acetate (150 mL). The organic layer was separated, washed with saturated salted water (15 mL), dried with anhydrous sodium sulfate, filtered and vacuum distilled, and the residue obtained was column chromatographed on silica gel (hexane/ethyl acetate (1:1.5)) to give methyl 3,4,5-tris(2-(2-(2-azidoethoxy)ethoxy)ethoxy)benzoate (2.18 g, 94%). $^1$H NMR (500 MHz, CDCl$_3$) δ 7.29 (s, 2H), 4.18-4.23 (m, 6H), 3.86-3.88 (m, 7H), 3.81 (t, 2H, J=5.0 Hz), 3.70-3.74 (m, 6H), 3.63-3.67 (m, 12H), 3.36-3.39 (m, 6H).

2-5. Synthesis of 3,4,5-Tris(2-(2-(2-azidoethoxy)ethoxy)ethoxy)benzoic Acid Compound of Chemical Formula 12

To a solution in which the 3,4,5-tris(2-(2-(2-azidoethoxy)ethoxy)ethoxy)benzoate (2.18 g, 3.32 mmol) of Chemical Formula 11 was dissolved in THF, water-soluble LiOH (1 M) (9.96 mL, 9.96 mmol) was added at room temperature, and the mixture was heated under reflux for 4 hours. The post-reaction mixture was cooled to room temperature, and was acidified to pH 4 by adding 0.1 N HCl. This mixture was partitioned to distilled water (40 mL) and ethyl acetate (100 mL), the organic layer was separated, washed with saturated salted water (15 mL), dried with anhydrous sodium sulfate, then filtered, and the resulting filtrate was vacuum distilled to give 3,4,5-tris(2-(2-(2-azidoethoxy)ethoxy)ethoxy)benzoic acid (2.90 g, 98%). $^1$H NMR (500 MHz, CDCl$_3$) δ 7.35 (s, 2H), 4.18-4.29 (m, 6H), 3.81-3.88 (m, 6H), 3.73 (m, 6H), 3.65-3.68 (m, 12H), 3.38 (m, 6H); $^{13}$C NMR (125 MHz, CDCl$_3$) δ 170.9, 152.4, 143.3, 124.0, 109.6, 72.5, 70.9 (3), 70.8 (3), 70.6, 70.1 (3), 69.8 (2), 68.9 (2), 50.7 (3).

2-6. Synthesis of Methyl 4-(Aminomethyl)benzoate Compound of Chemical Formula 13

The mixture of 4-(aminomethyl)benzoic acid (1.0 g, 6.61 mmol) and chlorotrimethylsilane (3.35 mL, 26.44 mmol) was stirred for 30 minutes at room temperature, and anhydrous methanol (20 mL) was added thereto. The reaction mixture was stirred for 48 hours and then vacuum distilled to give methyl 4-(aminomethyl)benzoate (1.25 g, 94%). $^1$H NMR (500 MHz, D$_2$O) δ 8.02 (d, 2H, J=6.4 Hz), 7.51 (d, 2H, J=8.2 Hz), 4.20 (s, 2H), 3.88 (s, 3H).

2-7. Synthesis of Methyl 4-((3,4,5-Tris(2-(2-(2-azidoethoxy)ethoxy)ethoxy)benzamido)methyl)benzoate Compound of Chemical Formula 14

To a solution in which the 3,4,5-tris(2-(2-(2-azidoethoxy)ethoxy)ethoxy)benzoic acid (1.29 g, 2.01 mmol) of Chemical Formula 12 was dissolved in methylene chloride (10 mL), methyl 4-(aminomethyl)benzoate (810 mg, 4.02 mmol) of Chemical Formula 13, triethylamine (1.17 mL, 8.4 mmol) and EDAC (770.6 mg, 4.02 mmol) were added in order. After the reaction mixture was stirred for 36 hours at room temperature, ethyl acetate (100 mL) was added thereto, the result was acidified using 0.5 N HCl (20 mL), and then the organic layer was separated by introducing distilled water (20 mL). The organic layer was washed with saturated salted water (10 mL), dried with anhydrous sodium sulfate, then filtered, and the resulting filtrate was vacuum distilled. The residue obtained was column chromatographed on silica gel (hexane/ ethyl acetate/methanol (4:4:1)) to give methyl 4-((3,4,5-tris(2-(2-(2-azidoethoxy)ethoxy)ethoxy) benzamido)methyl)benzoate (941 mg, 60%). $^1$H NMR (500 MHz, CDCl$_3$) δ 8.01 (d, 2H, J=8.2 Hz), 7.40 (d, 2H, J=8.2 Hz), 7.08 (s, 2H), 6.57 (bs, 1H), 4.67 (d, 2H, J=5.5 Hz), 4.20 (m, 6H), 3.90 (s, 3H), 3.84 (m, 4H), 3.80 (t, 2H, J=5.0 Hz), 3.68-3.71 (m, 6H), 3.63-3.65 (m, 12H), 3.33-3.38 (m, 6H); $^{13}$C NMR (125 MHz, CDCl$_3$) δ 166.9 (2), 152.6 (2), 143.6, 141.8, 130.1 (2), 129.4, 129.3, 127.7 (2), 107.3 (2), 72.4, 70.8 (3), 70.7 (3), 70.6, 70.1, 70.0 (2), 69.8 (2), 69.2 (2), 52.2, 50.7 (3), 43.8.

2-8. Synthesis of 4-((3,4,5-Tris(2-(2-(2-azidoethoxy)ethoxy)ethoxy)benzamido)methyl)benzoic Acid Compound of Chemical Formula 15

To a solution in which the methyl 4-((3,4,5-tris(2-(2-(2-azidoethoxy)ethoxy)ethoxy)benzamido)methyl) benzoate (930 mg, 1.17 mmol) of Chemical Formula 14 was dissolved in THF (10 mL), LiOH (1 M) (7.02 mL, 7.02 mmol) was added at room temperature, and then the mixture was stirred for 4 hours at the same temperature. The post-reaction mixture was acidified using 0.1 N HCl and the pH was lowered to 4. This mixture was partitioned to distilled water (30 mL) and ethyl acetate (100 mL). The organic layer was separated, washed with saturated salted water (15 mL), dried with anhydrous sodium sulfate, then filtered, and the resulting filtrate was vacuum distilled to give 4-((3,4,5-tris(2-(2-(2-azidoethoxy)ethoxy)ethoxy)benzamido)methyl)benzoic acid (897 mg, 99%). $^1$H NMR (500 MHz, CDCl$_3$) δ 8.04 (d, 2H, J=8.2 Hz), 7.42 (d, 2H, J=8.2 Hz), 7.10 (s, 2H), 6.65 (bs, 1H), 4.68 (d, 2H, J=4.6 Hz), 4.22 (m, 6H), 3.85 (t, 4H, J=4.6 Hz), 3.80 (t, 2H, J=5.0 Hz), 3.70-3.71 (m, 6H), 3.63-3.66 (m, 12H), 3.33-3.38 (m, 6H); $^{13}$C NMR (125 MHz, CDCl$_3$) δ 170.3, 167.1 152.6 (2), 144.4, 141.8, 130.6 (2), 129.2, 128.6, 127.7 (2), 107.4 (2), 72.4, 70.8 (3), 70.7 (3), 70.6, 70.1, 70.0 (2), 69.8 (2), 69.2 (2), 50.7 (3), 43.8.

2-9. Synthesis of 4-Methoxybenzyl 4-((3,4,5-Tris(2-(2-(2-azidoethoxy)ethoxy)ethoxy)benzamido)methyl)benzoate Compound of Chemical Formula 5

To a solution in which the 4-((3,4,5-tris(2-(2-(2-azidoethoxy)ethoxy)ethoxy)benzamido)methyl)benzoic acid (800 mg, 1.03 mmol) of Chemical Formula 15 was dissolved in DMF (8 mL), para-methoxy benzyl bromide (0.22 mL, 1.54 mmol) and sodium bicarbonate (346.1 mg, 4.12 mmol) were added in order, and then the mixture was stirred for 10 hours. The post-reaction mixture was partitioned to distilled water (50 mL) and ethyl acetate (100 mL), and then the organic layer was separated. The separated organic layer was washed with saturated salted water (10 mL), dried with anhydrous sodium sulfate, then filtered, and the resulting filtrate was vacuum distilled. The residue obtained was column chromatographed on silica gel (hexane/ethyl acetate/methanol (6:6:1)) to give 4-methoxy benzyl 4-((3,4,5-tris(2-(2-(2-azidoethoxy)ethoxy) ethoxy)benzamido)methyl)benzoate (755.8 mg, 82%). $^1$H NMR (500 MHz, CDCl$_3$) δ 8.02 (d, 2H, J=8.7 Hz), 7.37 (t, 4H, J=8.2 Hz), 7.07 (s, 2H), 6.90 (m, 2H), 6.59 (t, 1H, J=5.9 Hz), 5.28 (s, 2H), 4.65 (d, 2H, J=5.9 Hz), 4.19 (t, 6H, J=5.0 Hz), 3.84 (t, 4H, J=5.0 Hz), 3.80 (s, 3H), 3.79 (m, 2H), 3.69-3.71 (m, 6H), 3.62-3.65 (m, 12H), 3.32-3.37 (m, 6H).
$^{13}$C NMR (125 MHz, CDCl$_3$) δ 166.9, 166.3, 159.7, 152.6 (2), 143.7, 141.7, 130.2 (2), 130.1 (2), 129.5, 129.3, 128.1, 127.7 (2), 114.0 (2), 107.3 (2), 72.4, 70.8 (3), 70.7 (3), 70.6, 70.1, 70.0 (2), 69.8 (2), 69.2 (2), 66.6, 55.3, 50.7 (3), 43.8.

EXAMPLE 3

Synthesis of Succinimidyl Ester of Coumarin Dendrimer Multi-fluorescent Substance of Chemical Formula 6 (Coumarin-trimolecular Fluorescent Substance)

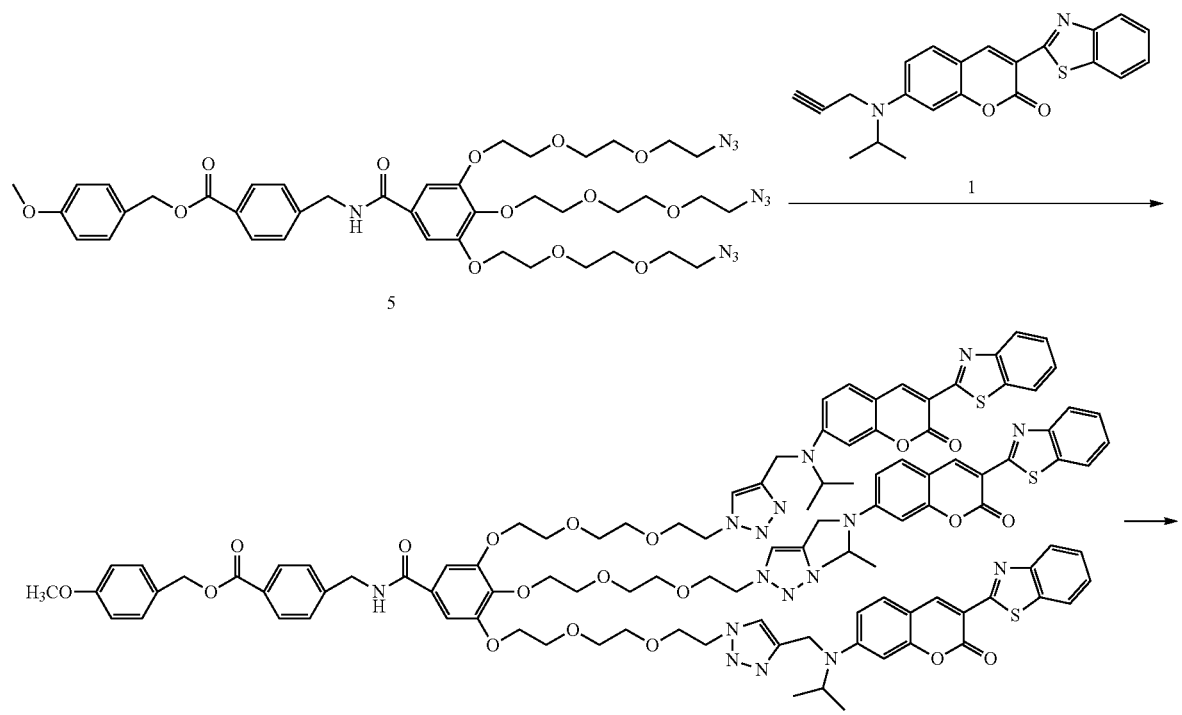

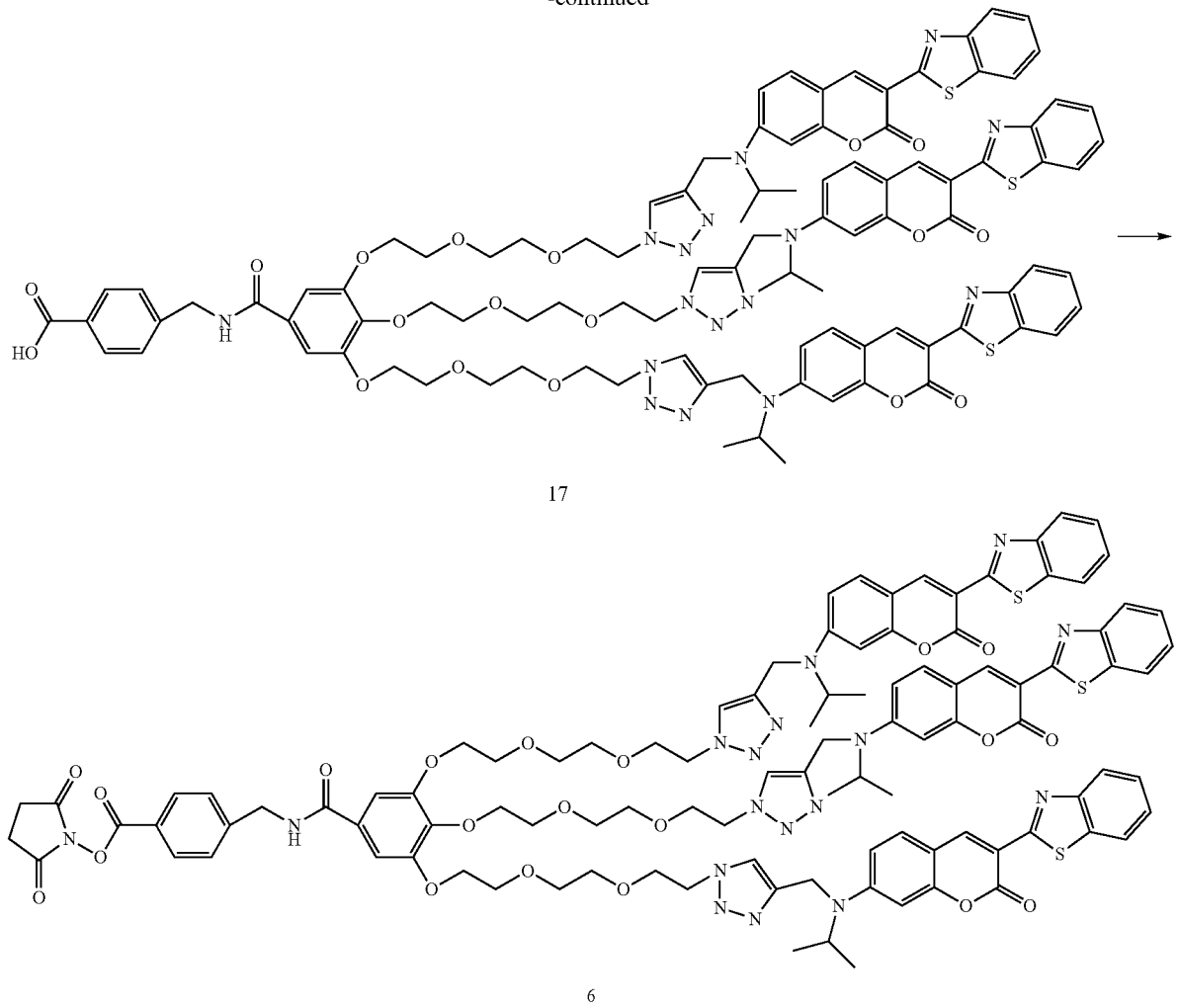

Synthesis processes of a succinimidyl ester of coumarin dendrimer multi-fluorescent substance are as follows.

3-1. Synthesis of 4-Methoxybenzyl 4-((3,4,5-Tris(2-(2-((4-(((3-(benzo[d]thiazol-2-yl)-2-oxo-2H-chromen-7-yl)(isopropyl)amino)methyl)-1H-1,2,3-triazol-1-yl)methoxy)ethoxy)ethoxy)benzamido)methyl)benzoate Compound of Chemical Formula 16

After the 3-(benzo[d]thiazol-2-yl)-7-(isopropyl(prop-2-ynyl)amino)-2H-chromen-2-one (164.7 mg, 0.44 mmol) compound of Chemical Formula 1 and the 4-methoxy benzyl 4-((3,4,5-tris(2-(2-(2-azidoethoxy)ethoxy) ethoxy)benzamido)methyl)benzoate (100 mg, 0.11 mmol) compound of Chemical Formula 5 were mixed with methylene chloride (2 mL) and distilled water (1 mL), and $CuSO_4 \cdot 5H_2O$ (4.2 mg, 15 mol %) and sodium ascorbate (9.9 mg, 45 mol %) were added in order thereto at room temperature, the mixture was stirred for 8 hours. The post-reaction mixture was partitioned to distilled water (30 mL) and methylene chloride (50 mL), and the organic layer was separated. The organic layer was washed with saturated salted water (10 mL), dried with anhydrous sodium sulfate, the filtered, and the resulting filtrate was vacuum distilled. The residue obtained was column chromatographed on silica gel (chloroform/methanol (20:1)) to give 4-methoxybenzyl 4-((3,4,5-tris(2-(2-((4-(((3-(benzo[d]thiazol-2-yl)-2-oxo-2H-chromen-7-yl)(isopropyl)amino)methyl)-1H-1,2,3-triazol-1-yl)methoxy)ethoxy) ethoxy)benzamido)methyl)benzoate (130.4 mg, 60%). $^1$H NMR (500 MHz), $CDCl_3$) δ 9.17 (s, 3H), 8.06 (d, 2H, J=7.3 Hz), 7.86 (d, 3H, J=7.8 Hz), 7.76 (d, 3H, J=7.7 Hz), 7.48 (m, 4H), 7.35-7.39 (m, 9H), 7.30 (d, 3H, J=7.8 Hz), 7.18 (s, 2H), 6.89 (d, 2H, J=8.7 Hz), 6.71 (d, 3H, J=7.8 Hz), 6.58 (s, 3H), 5.22 (s, 2H), 4.47-4.61 (m, 14H), 4.23 (m, 3H), 4.01-4.03 (m, 6H), 3.79 (m, 9H), 3.62 (m, 6H), 3.48-3.52 (m, 12H), 1.25 (d, 18H, J=6.4 Hz).

3-2. Synthesis of 4-((3,4,5-Tris(2-(2-((4-(((3-(benzo[d]thiazol-2-yl)-2-oxo-2H-chromen-7-yl)(isopropyl)amino)methyl)-1H-1,2,3-triazol-1-yl)methoxy)ethoxy) ethoxy)benzamido)methyl)benzoic Acid Compound of Chemical Formula 17

To a solution in which the 4-methoxybenzyl 4-((3,4,5-tris (2-(2-((4-(((3-(benzo[d]thiazol-2-yl)-2-oxo-2H-chromen-7-yl)(isopropyl)amino)methyl)-1H-1,2,3-triazol-1-yl)methoxy)ethoxy) ethoxy)benzamido)methyl)benzoate (120 mg, 0.06 mmol) compound of Chemical Formula 16 was dissolved in methylene chloride (2 mL), trifluoroacetic acid (1 mL) was added at room temperature, and the mixture was stirred for 36 hours at the same temperature. Ethanol (10 mL) was added together when the post-reaction mixture was vacuum distilled to remove trifluoroacetic acid. This vacuum distillation was repeated 6 times to give 4-((3,4,5-tris(2-(2-((4-(((3-(benzo[d]thiazol-2-yl)-2-oxo-2H-chromen-7-yl)(isopropyl)amino)methyl)-1H-1,2,3-triazol-1-yl)methoxy)ethoxy) ethoxy)benzamido)methyl)benzoic acid (105.7 mg, 95%), and the product was immediately used for the next reaction without further purification.

3-3. Synthesis of 2,5-Dioxopyrrolidin-1-yl 4-((3,4,5-tris(2-(2-((4-(((3-(benzo[d]thiazol-2-yl)-2-oxo-2H-chromen-7-yl)(isopropyl)amino)methyl)-1H-1,2,3-triazol-1-yl)methoxy)ethoxy)ethoxy)benzamido)methyl)benzoate Compound of Chemical Formula 6

To a solution in which the 4-((3,4,5-tris(2-(2-((4-(((3-(benzo[d]thiazol-2-yl)-2-oxo-2H-chromen-7-yl)(isopropyl)amino)methyl)-1H-1,2,3-triazol-1-yl)methoxy)ethoxy)ethoxy)benzamido)methyl)benzoic acid (100 mg, 0.053 mmol) compound of Chemical Formula 17 was dissolved in methylene chloride (2 mL), N-hydroxy succinimide (243.9 mg, 2.12 mmol) and EDAC (406.4 mg, 2.12 mmol) were added in order at 0° C., and the mixture was stirred overnight at room temperature. After the post-reaction mixture was partitioned to methylene chloride (20 mL) and distilled water (20 mL), the separated organic layer was washed with saturated salted water (10 mL), dried with anhydrous sodium sulfate, then filtered, and the resulting filtrate was vacuum distilled. The residue obtained was column chromatographed on silica gel (chloroform/methanol (20:1)) to give 2,5-dioxopyrrolidin-1-yl 4-((3,4,5-tris(2-(2-((4-(((3-(benzo[d]thiazol-2-yl)-2-oxo-2H-chromen-7-yl)(isopropyl)amino)methyl)-1H-1,2,3-triazol-1-yl)methoxy)ethoxy)ethoxy)benz amido)methyl)benzoate (96 mg, 92%). $^1$H NMR (500 MHz, CDCl$_3$) δ 10.04 (s, 3H), 8.32 (d, 2H, J=8.2 Hz), 8.11 (d, 3H, J=9.6 Hz), 7.93 (d, 4H, J=7.3 Hz), 7.74 (d, 3H, J=7.3 Hz), 7.45-7.60 (m, 9H), 7.37 (m, 3H), 6.82 (m, 3H), 6.65 (s, 3H), 4.53-4.70 (m, 14H), 4.34 (m, 3H), 4.01-4.13 (m, 6H), 3.82 (m, 9H), 3.65 (m, 6H), 3.52 (m, 12H), 2.91 (s, 4H), 1.25 (d, 18H, J=6.4 Hz).

EXAMPLE 4

Analysis on Optimal Wavelength of Coumarin Multi-fluorescent Substance (Coumarin-trimolecular Fluorescent Substance)

Figure 2:
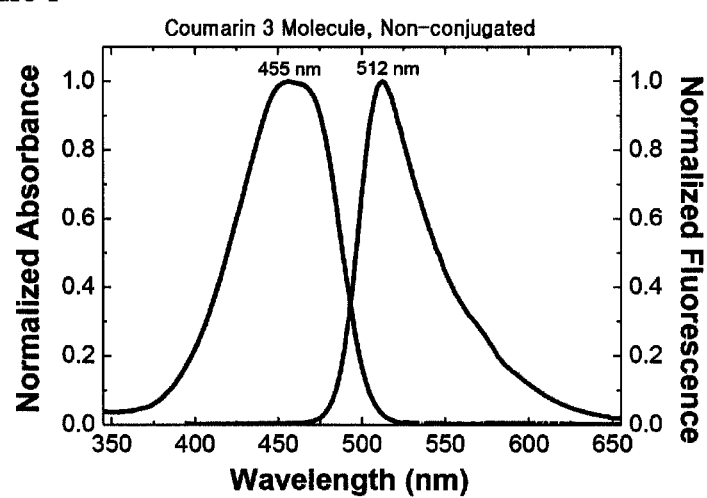
FIG. 2 shows the result of measuring an optimal wavelength of a coumarin-trimolecular fluorescent substance.

The optimal excitation and the light emission wavelength of the synthesized coumarin multi-fluorescent substance were analyzed. The coumarin multi-fluorescent substance was dissolved in a DMSO solution to have a concentration of 1 mg/ml, and the light emission and the excitation spectra were analyzed. The analysis result showed that the coumarin multi-fluorescent substance (coumarin-trimolecular fluorescent substance) had an excitation wavelength of 455 nm and a light emission wavelength of 512 nm, as shown in FIG. 2.

EXAMPLE 5

Analysis on Optimal Synthesis Condition of Coumarin-trimolecular Fluorescent Substance-Antibody Conjugation Product Through Fluorescence-linked Immunosorbent Assay (FLISA)

0.5 ml (0.5 mg/ml) of a monoclonal antibody (mal-D2H) was mixed with 0.5 ml of a 0.1 M NaHCO$_3$ (pH 9.2) buffer solution to form a proper pH, and the mixture was stabilized for 4 hours at room temperature. 1 ml of the mixed liquid was mixed with the coumarin-trimolecular fluorescent substance in a concentration gradient manner so that the number of moles of the coumarin-trimolecular fluorescent substance (1 mg/ml) prepared in Example 3 was 10 times (66 µl), 8 times (53 µl), 6 times (40 µl) and 4 times (26 µl) each with respect to the antibody, and conjugation was induced by reacting them for 10 hours at 4° C. In the reaction solution, the unreacted fluorescent substance molecules were removed through dialysis, and the fluorescent substance-antibody conjugation product was purified. The concentration of the antibody-fluorescent substance conjugation product of the eluents was measured by measuring the protein concentration.

In order to establish an optimal conjugation condition, a fluorescence-linked immunosorbent assay was carried out for normal patients and malaria-infected patients using the purified coumarin-trimolecular fluorescent substance-antibody conjugation product. A monoclonal antibody (mal-D7E) was mixed with a carbonate buffer solution (carbonate/bicarbonate coating buffer), 0.5 µg or 1 µg of the antibody was placed in each well of a 96-well black plate for FLISA, and was fixed for 18 hours at 4° C. The result was washed with a phosphate buffer solution (PBS, 0.1% tween-20), treated with a blocking buffer, and the result was reacted for 1 hour at 37° C. The result was washed with a phosphate buffer solution (PBS, 0.1% tween-20), and 2 µl each of the blood of *Plasmodium vivax* (Pv) patients and normal patients prepared in advance was mixed with 200 µl of a phosphate buffer solution (PBS) (1:100 dilution) and then placed in each plate well, and the mixture was reacted for 1 hour at 37° C. The result was washed with a phosphate buffer solution (PBS, 0.1% tween-20), 100 µl each of the fluorescent substance-antibody (mal-D2H) conjugation product (10 equivalents, 8 equivalents, 6 equivalents, 4 equivalents) was added thereto, and the result was reacted for 1 hour at 37° C. After the result was washed with a phosphate buffer solution (PBS, 0.1% tween-20), the fluorescence was measured using the excitation wavelength (excitation 460 nm, bandwidth 20 nm) and the light emission wavelength (emission 505 nm, bandwidth 10 nm). The optimal conjugation condition of the monoclonal antibody-fluorescent substance conjugation product was analyzed by analyzing the fluorescence intensity (relative fluorescence).

Figure 3:
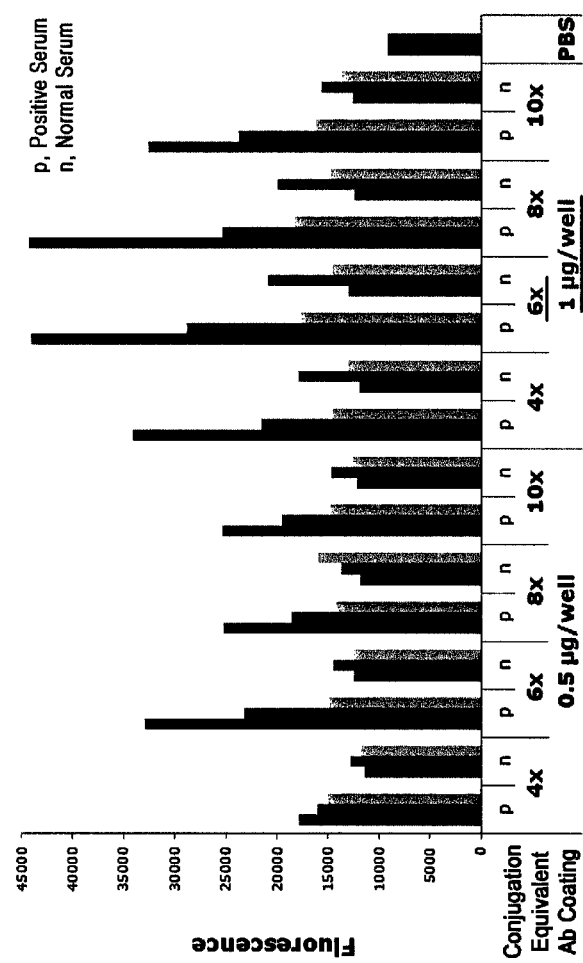
FIG. 3 shows an optimal conjugation ratio of a coumarin-trimolecular fluorescent substance-antibody conjugation product through an optimized FLISA.

As shown in FIG. 3, the coumarin-trimolecular fluorescent substance-antibody conjugation product exhibited high reactivity for malaria antigens, and particularly, normal patients and malaria-infected patients were most sharply distinguished when the conjugation was 6× equivalents, and when 1 µg of the antibody (mal-D7E) was coated on the well.

EXAMPLE 6

Figure 4:
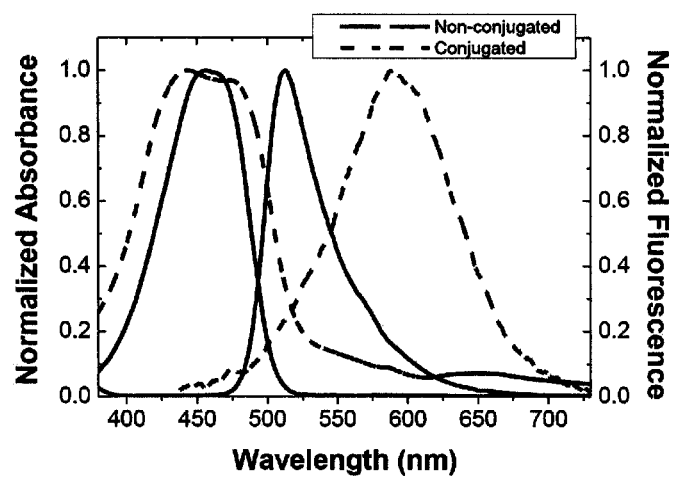
FIG. 4 shows the result of measuring an optimal wavelength of a coumarin-trimolecular fluorescent substance-antibody conjugation product.

Analysis on Optimal Wavelength of Coumarin Multi-Fluorescent Substance-Monoclonal Antibody Conjugation Product The optimal light emission and the excitation spectra when the coumarin multi-fluorescent substance was conjugated with a monoclonal antibody were analyzed using the method as in Example 4. The conjugation was carried out in 6× equivalents of the antibody as in Example 5. It was seen from the analysis results on the optimal spectra of the fluorescent substance-antibody conjugation product that, as in FIG. 4, the light excitation wavelength did not change, however, the emission wavelength significantly changed to 590 nm (FIG. 4).

EXAMPLE 7

Evaluation on Clinical Usefulness of Fluorescence-linked Immunosorbent Assay in Optimal Wavelength of Fluorescent Substance-Antibody A fluorescence-linked immunosorbent assay (FLISA) was carried out using the blood of patients in order to evaluate the clinical usefulness for the reactivity of the monoclonal antibody-fluorescent substance conjugation product in the optimal light emission wavelength of the fluorescent substance-antibody conjugation product. A monoclonal antibody (mal-D7E) was mixed with a carbonate buffer solution (carbonate/bicarbonate coating buffer), 1 µg of the antibody was placed in each well of a 96-well black plate for FLISA, and was fixed for 18 hours at 4° C. The result was washed with a phosphate buffer solution (PBS, 0.1% tween-20), treated with 200 µl of a blocking buffer, and the result was reacted for 1 hour at 37° C. After the result was washed with a phosphate buffer solution (PBS, 0.1% tween-20), 2 µl each of the blood of *Plasmodium vivax* (Pv) patients, *Plasmodium falciparum* (Pf) patients and normal patients prepared was mixed with 200 µl of a phosphate buffer solution (PBS) (1:100 dilution) and then placed in each plate well, and the mixture was reacted for 1 hour at 37° C. The result was washed with a phosphate buffer solution (PBS, 0.1% tween-20), 100 µl each of the fluorescent substance-antibody (mal-D2H) conjugation product (6× equivalents) was added thereto, and the result was reacted for 1 hour at 37° C. After the result was washed with a phosphate buffer solution (PBS, 0.1% tween-20), the fluorescent was measured using the excitation wavelength (excitation 460 nm, bandwidth 20 nm) and the light emission wavelength (emission 505 nm, bandwidth 10 nm). The infection status was analyzed by analyzing the fluorescence intensity (relative fluorescence) of the monoclonal antibody-fluorescent substance conjugation product for the blood of the malaria-infected patients with respect to the blood of the normal patients.

Figure 5:
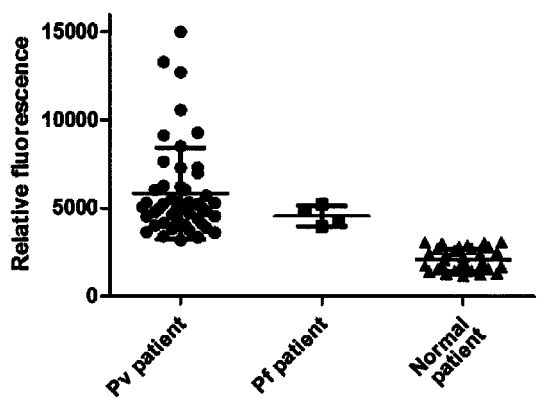
FIG. 5 shows the result of a FLISA test carried out with the blood of malaria-infected patients using a fluorescent substance-antibody conjugation product at an optimal wavelength of a coumarin-3 molecule fluorescent substance.

The coumarin-trimolecular fluorescent substance-antibody conjugation product exhibited high reactivity for the blood of the malaria patients (FIG. 5). The infection status of the malaria-infected patients was confirmed by microscope observation, gene diagnosis (PCR) and rapid diagnostic kit diagnosis, and as a result of the fluorescence-linked immunosorbent assay, 50 *Plasmodium vivax* patients, 4 *Plasmodium falciparum* patients were all confirmed to be positively diagnosed based on the average of relative fluorescence value for the 34 normal patient samples, therefore, diagnosis sensitivity of 100% was obtained (FIG. 5).

The relative fluorescence value for the 34 normal patient samples was measured as 2079.5±628 (average value±standard deviation), therefore, the value may be used as a number algorithm that distinguishes infection positive and negative when a microfluorescent quantitative biosensor for diagnosis is developed.

EXAMPLE 8

Carrying Out of Rapid Fluorescent Immunochromatographic Test (FICT)

Figure 6:
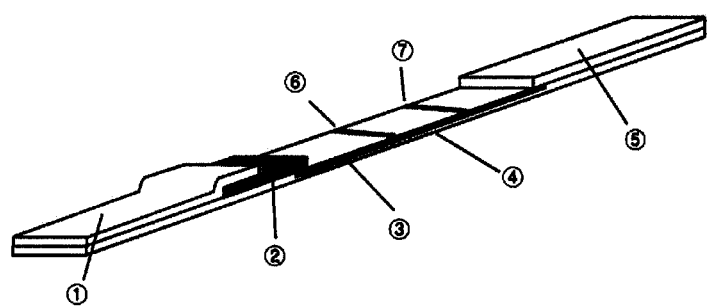
FIG. 6 shows a drawing of a rapid fluorescent immunochromatographic test (FICT) using a coumarin-trimolecular fluorescent substance-antibody conjugation product. The references described in the drawing mean ① absorption pad, ② conjugation pad, ③ nitrocellulose membrane, ④ plastic supporter, ⑤ absorption pad, ⑥ test line, and ⑦ control line.

In order to verify the applicability of the monoclonal antibody-fluorescent substance conjugation product to a rapid fluorescent immunochromatographic test (FICT) that is useful for the development of a biosensor for field diagnosis, a rapid fluorescent immunochromatographic test (FICT) was carried out. As in FIG. 6, a monoclonal antibody (mal-D7E) was mixed with a phosphate buffer solution (phosphate buffered saline) and the mixture was placed to the test line location of a nitrocellulose membrane at a concentration of 2.0 mg/ml. A goat anti mouse IgG antibody was divided to the control line area at a concentration of 1.5 mg/ml, and then this membrane was fixed for 2 days at 37° C. A pad made of cotton was partially overlapped at the top area of the membrane, and a conjugation pad and a specimen pad were partially overlapped at the bottom area, and then were installed.

After the specimen was developed on the membrane phase by placing 10 µl of the prepared malaria adjuvant in a specimen injection area, and additionally adding 100 µl of a specimen developing liquid (phosphate buffer solution, 0.1% Tween 20, 0.02% Casein) thereto, reading was made after 15 minutes had passed. As the reading, fluorescence needs to be measured at the light emission wavelength (emission 560 nm, bandwidth 20 nm) after absorbing light at the excitation wavelength (excitation 460 nm, bandwidth 20 nm) of the coumarin that reacted to the strip. However, in this example, the fluorescence of the reacted coumarin was strong sufficient to be observed with the naked eye from outside, therefore, the reactivity of the monoclonal antibody-fluorescent substance conjugation product for the malaria adjuvant was observed with the naked eye.

Figure 7:
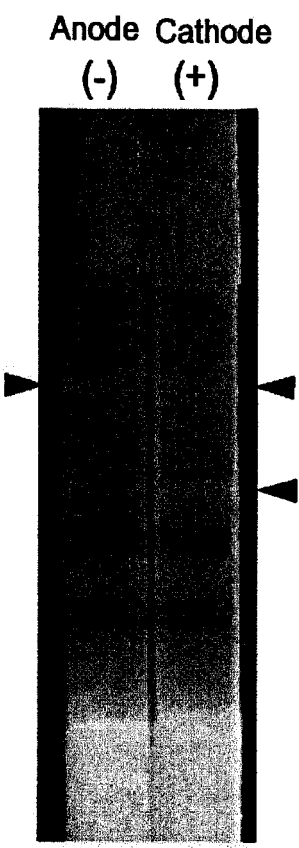
FIG. 7 shows the result of a rapid fluorescent immunochromatographic test (FICT) carried out with the blood of malaria-infected patients using a coumarin-trimolecular fluorescent substance-antibody conjugation product.

As in FIG. 7, the coumarin-trimolecular fluorescent substance-antibody conjugation product exhibited high reactivity for malaria antigens. In other words, in the area in which the malaria-negative specimen was injected, fluorescence did not appear at the test line location, and in the area in which the malaria-positive specimen was injected, a strong fluorescence signal was observed with the naked eye at the test line location.

The invention claimed is:

1. A succinimidyl ester of coumarin dendrimer represented by Chemical Formula 6 and which is a multi-fluorescent substance:

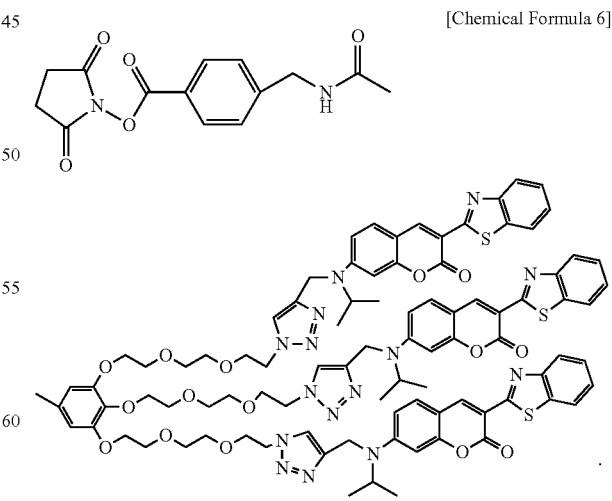

[Chemical Formula 6]

2. A succinimidyl ester of coumarin dendrimer represented by Chemical Formula 19 and which is a multi-fluorescent substance:

[Chemical Formula 19]
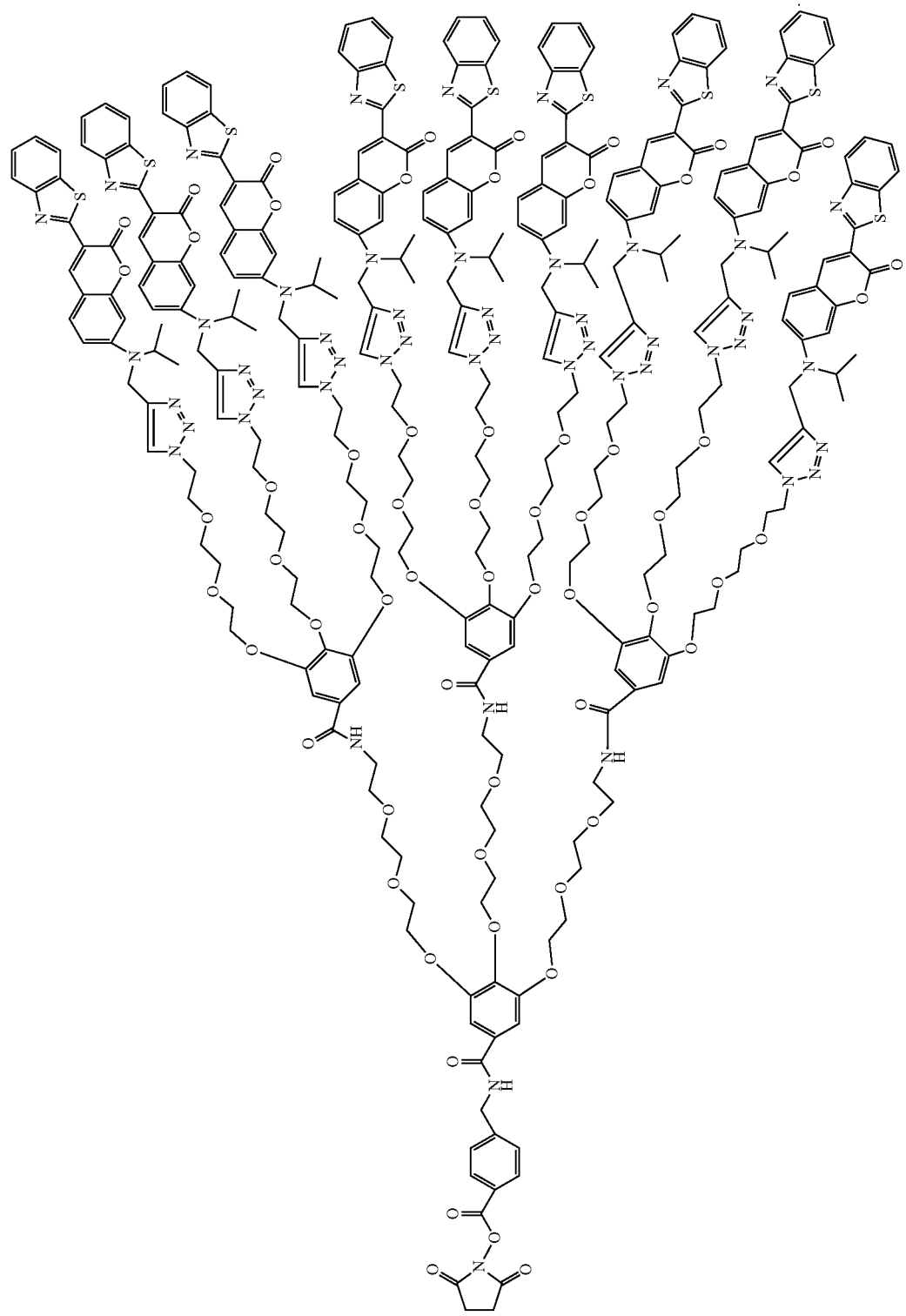

3. A succinimidyl ester of coumarin dendrimer represented by Chemical Formula 21 and which is a multi-fluorescent substance:

[Chemical Formula 21]
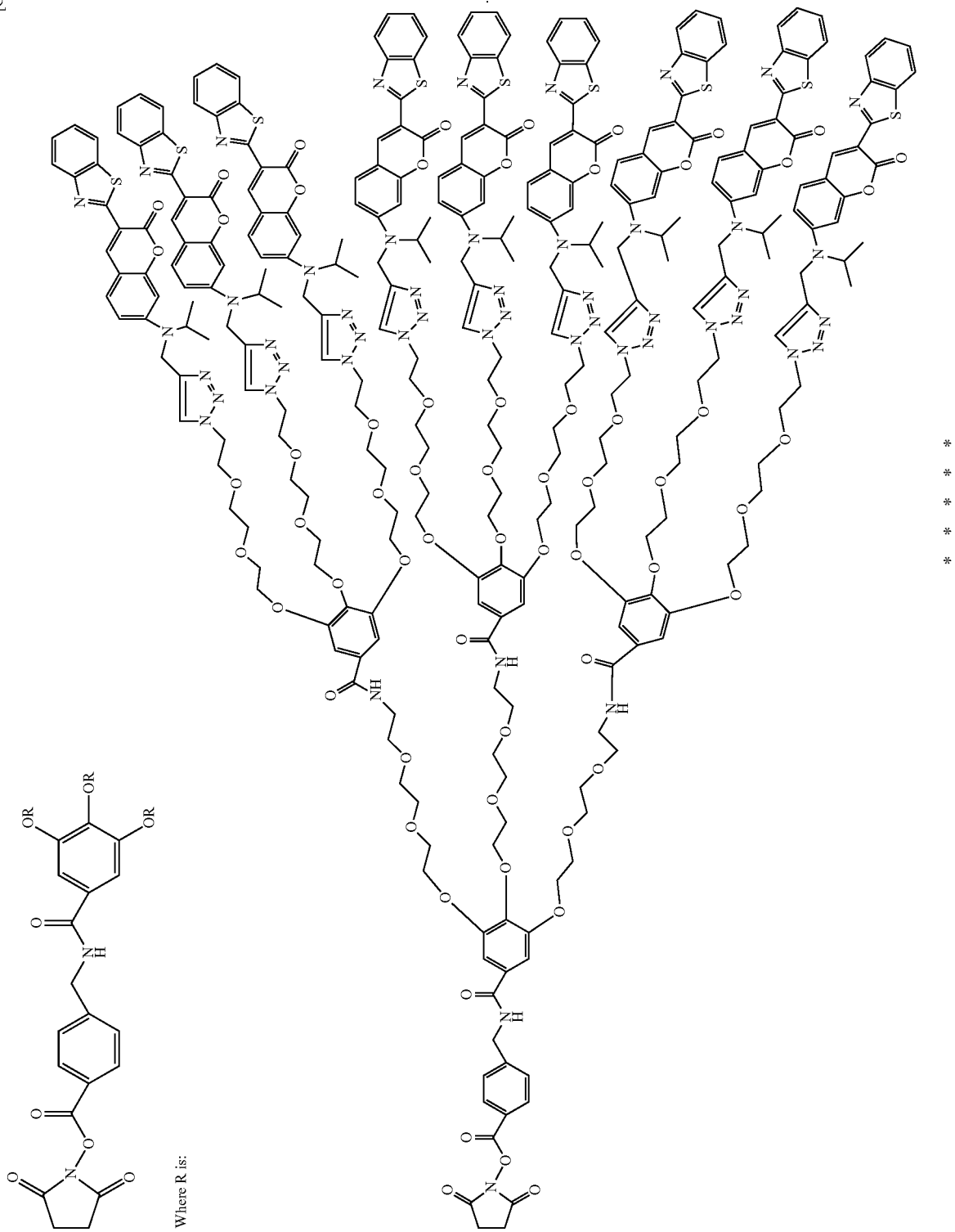
Where R is: